US012629688B2

(12) United States Patent
Mcfall et al.

(10) Patent No.: US 12,629,688 B2
(45) Date of Patent: May 19, 2026

(54) DEVICES AND METHODS FOR RAPID SAMPLE PROCESSING AND ANALYSIS

(71) Applicant: Northwestern University, Evanston, IL (US)

(72) Inventors: Sally Maureen Mcfall, Evanston, IL (US); David M. Kelso, Wilmette, IL (US); Jennifer Lynn Reed, Chicago, IL (US); Tom Westberg, Gurnee, IL (US)

(73) Assignee: Northwestern University, Evanston, IL (US)

( * ) Notice: Subject to any disclaimer, the term of this patent is extended or adjusted under 35 U.S.C. 154(b) by 171 days.

(21) Appl. No.: 18/428,532

(22) Filed: Jan. 31, 2024

(65) Prior Publication Data

US 2024/0173719 A1 May 30, 2024

Related U.S. Application Data

(63) Continuation of application No. 16/615,630, filed as application No. PCT/US2018/034443 on May 24, 2018, now Pat. No. 12,269,040.

(Continued)

(51) Int. Cl.
| | |
|---|---|
| *B01L 7/00* | (2006.01) |
| *B01L 3/00* | (2006.01) |
| *C12Q 1/686* | (2018.01) |
| *G01N 1/28* | (2006.01) |
| *G01N 21/64* | (2006.01) |

(Continued)

(52) U.S. Cl.
CPC ....... *B01L 7/5255* (2013.01); *B01L 3/502715* (2013.01); *B01L 3/52* (2013.01); *C12Q 1/686* (2013.01); *G01N 1/28* (2013.01); *G01N 21/645* (2013.01); *G01N 35/0099* (2013.01);

*G01N 35/04* (2013.01); *B01L 2200/0684* (2013.01); *B01L 2300/0887* (2013.01); *B01L 2300/1827* (2013.01)

(58) Field of Classification Search
None
See application file for complete search history.

(56) References Cited

U.S. PATENT DOCUMENTS

| | | | |
|---|---|---|---|
| 3,882,619 A | 5/1975 | Durand |
| 4,683,195 A | 7/1987 | Mullis et al. |

(Continued)

FOREIGN PATENT DOCUMENTS

| | | |
|---|---|---|
| CN | 103820306 A | 5/2014 |
| EP | 0684315 | 6/2002 |

(Continued)

OTHER PUBLICATIONS

Gibson et al., A novel method for real time quantitative RT-PCR. Genome Res. Oct. 1996;6(10):995-1001.

(Continued)

*Primary Examiner* — Neil N Turk
(74) *Attorney, Agent, or Firm* — David W. Staple; Casimir Jones, S.C.

(57) ABSTRACT

Provided herein are devices and methods for the rapid processing and analysis of samples. In particular, a small-volume sample (e.g., nucleic acid sample) is exposed to (e.g., contacted with) different temperature zones within a device to process (e.g., amplify) and/or analyze (e.g., quantitate) the sample in an assay.

7 Claims, 29 Drawing Sheets

Related U.S. Application Data

(60) Provisional application No. 62/510,503, filed on May 24, 2017.

(51) Int. Cl.
*G01N 35/00* (2006.01)
*G01N 35/04* (2006.01)

(56) References Cited

U.S. PATENT DOCUMENTS

| | | | |
|---|---|---|---|
| 4,683,202 A | 7/1987 | Mullis | |
| 4,800,159 A | 1/1989 | Mullis et al. | |
| 4,941,753 A | 7/1990 | Wickramasinghe | |
| 4,965,188 A | 10/1990 | Mullis et al. | |
| 5,270,184 A | 12/1993 | Walker et al. | |
| 5,455,166 A | 10/1995 | Walker | |
| 5,460,780 A * | 10/1995 | Devaney, Jr. | G01N 35/00 |
| | | | 422/68.1 |
| 5,948,673 A | 9/1999 | Cottingham | |
| 6,605,294 B2 | 8/2003 | Sawhney | |
| 7,030,340 B2 | 4/2006 | Knoche | |
| 2004/0209331 A1 | 10/2004 | Ririe | |
| 2008/0286150 A1 | 11/2008 | Pankow | |
| 2009/0189752 A1 | 7/2009 | Taylor | |
| 2009/0241640 A1 | 10/2009 | Kallmes | |
| 2010/0167288 A1* | 7/2010 | Gale | B01L 7/54 |
| | | | 435/6.19 |
| 2010/0210006 A1 | 8/2010 | Spangler | |
| 2011/0207121 A1 | 8/2011 | Chen | |
| 2011/0212446 A1* | 9/2011 | Wang | C12Q 1/6858 |
| | | | 435/6.12 |
| 2011/0244522 A1 | 10/2011 | Seo et al. | |
| 2014/0038272 A1 | 2/2014 | Ririe | |

FOREIGN PATENT DOCUMENTS

| | | |
|---|---|---|
| EP | 0881950 B1 | 7/2004 |
| JP | 2004-535200 | 11/2004 |
| JP | 2014-515271 | 6/2014 |
| WO | WO 92/04979 A1 | 4/1992 |
| WO | WO 2012/161566 A1 | 11/2012 |
| WO | WO 2016/106717 A1 | 7/2016 |
| WO | WO 2018/218053 A1 | 11/2018 |

OTHER PUBLICATIONS

Heid et al.,Real time quantitative PCR. Genome Res. Oct. 1996;6(10):986-94.

Higuchi et al., Simultaneous Amplification and Detection of Specific DNA Sequences. Bio/Technology 10:413-417, 1992.

Higuchi et al., Kinetic PCR analysis: real-time monitoring of DNA amplification reactions. Biotechnology (N Y). Sep. 1993;11(9):1026-30.

Holland et al., Detection of specific polymerase chain reaction product by utilizing the 5'----3' exonuclease activity of Thermus aquaticus DNA polymerase. Proc Natl Acad Sci U S A. Aug. 15, 1991;88(16):7276-80.

Ishiguro et at., Homogeneous quantitative assay of hepatitis C virus RNA by polymerase chain reaction in the presence of a fluorescent intercalater. Anal Biochem. Aug. 10, 1995;229(2):207-13.

Nazarenko et al., A closed tube format for amplification and detection of DNA based on energy transfer. Nucleic Acids Res. Jun. 15, 1997;25(12):2516-21.

Nazarenko et al., Multiplex quantitative PCR using self-quenched primers labeled with a single fluorophore. 2002. Nucleic. Acids Res. vol. 30, Is 9, p. e37.

Omidian et al., Advances in superporous hydrogels. J Control Release. Jan. 20, 2005;102(1):3-12.

Park, et al., Biodegradable Hydrogels for Drug Delivery. 1993. Technomic Pub. Co., Lancaster, Pa.

Persing et al., In Vitro Nucleic Acid Amplification Techniques in Diagnostic Medical Microbiology: Principles and Applications. American Society for Microbiology, Washington, DC 1993 pp. 51-87.

Shin et al., Chemical structure and physical properties of cyclic olefin copolymers. 2005. Pure Appl. Chem., vol. 77, No. 5, pp. 801-814.

Tyagi et al., Molecular beacons: probes that fluoresce upon hybridization. Nat Biotechnol. Mar. 1996;14(3):303-8.

Vogelstein et al., Digital PCR. Proc Natl Acad Sci U S A. Aug. 3, 1999;96(16):9236-41.

Walker et al., Isothermal in vitro amplification of DNA by a restriction enzyme/DNA polymerase system. Proc Natl Acad Sci U S A. Jan. 1, 1992;89(1):392-6.

Weiss, Hot prospect for new gene amplifier. Science. Nov. 29, 1991;254(5036):1292-3.

Wittwer et al., Continuous fluorescence monitoring of rapid cycle DNA amplification. Biotechniques. Jan. 1997;22(1):130-1, 134-8.

International Search Report and Written Opinion for PCT/US18/34443. Mailed Oct. 22, 2018. 14 pages.

Extended European Search Report. PCT/US2018034443. Nov. 5, 2021. 12 Pages.

* cited by examiner

FIG. 3A
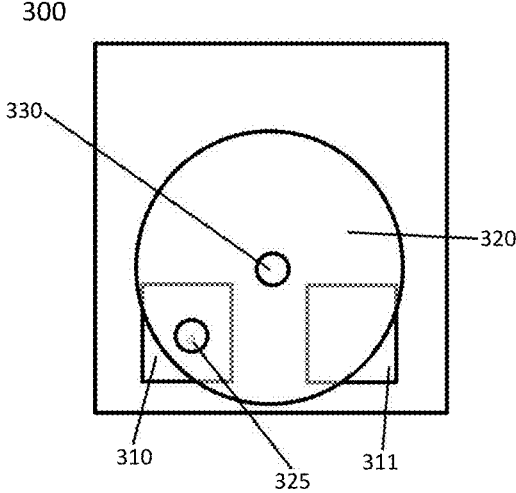
300
330
320
310    325    311
FIG. 3B
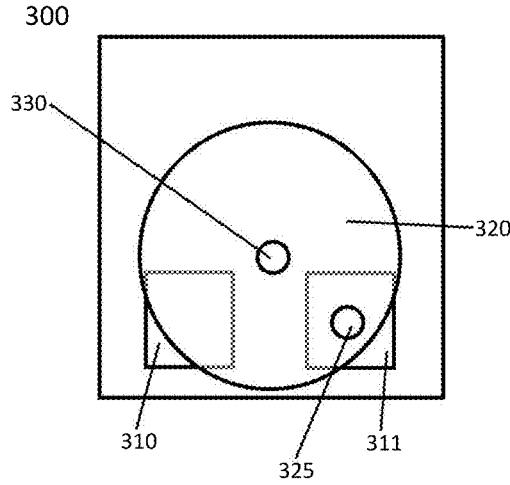
300
330
320
310    325    311

FIG. 4 A-C
A)
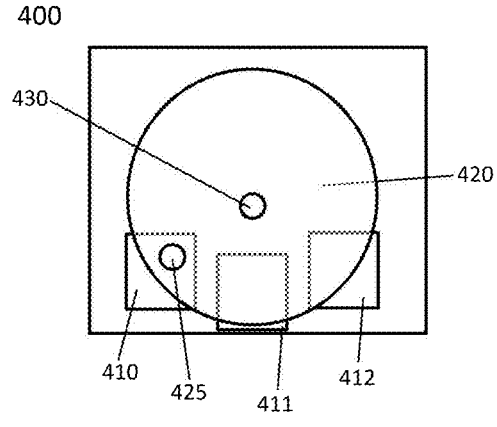
B)
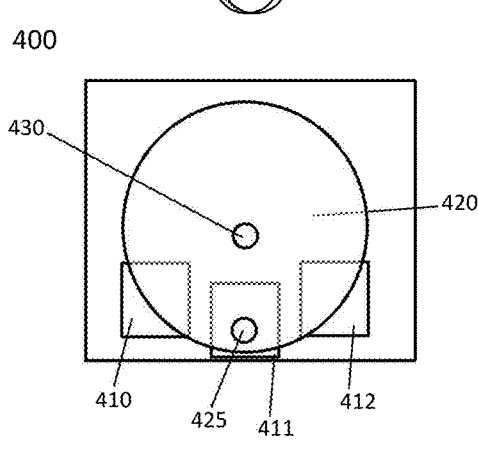
C)
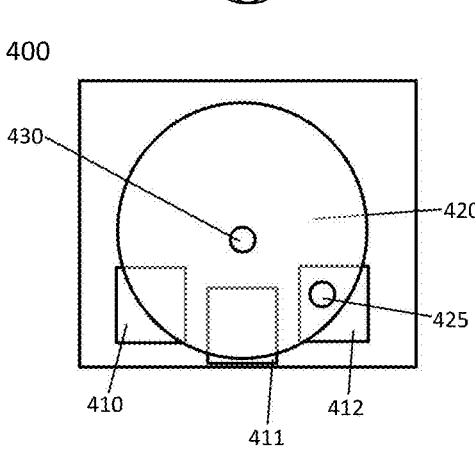

FIG. 5 A-C
A)
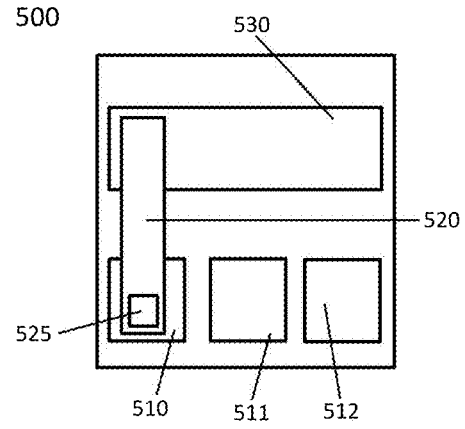
B)
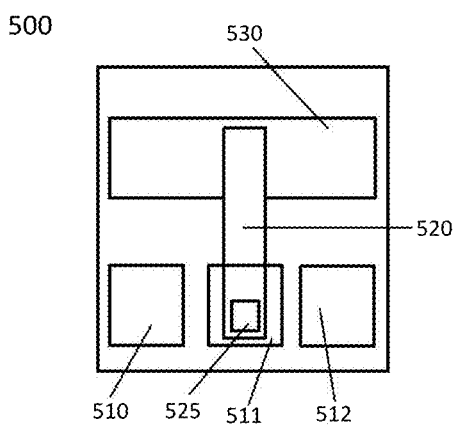
C)
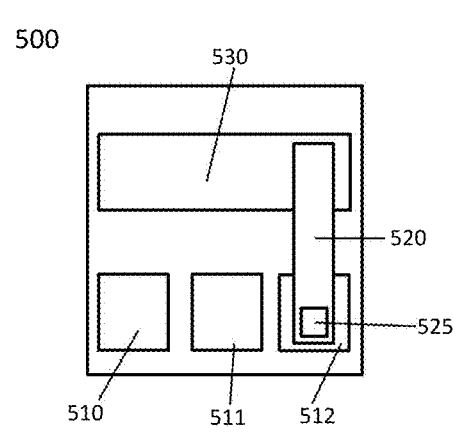

FIG. 6A-B
A)
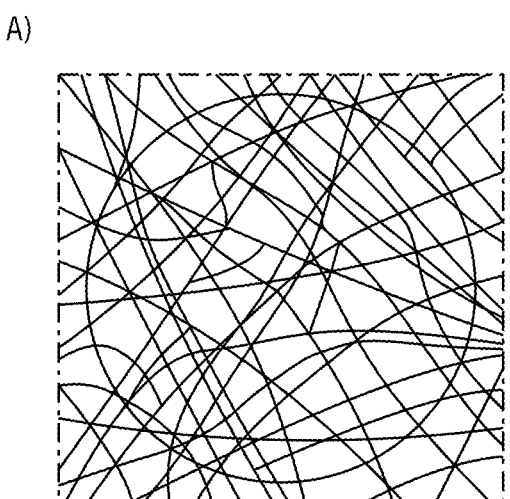
B)
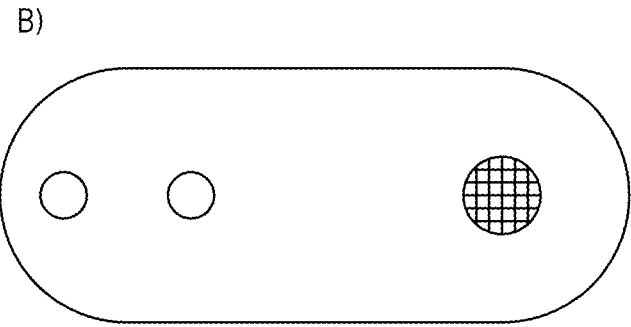

FIG. 7A–C
A)
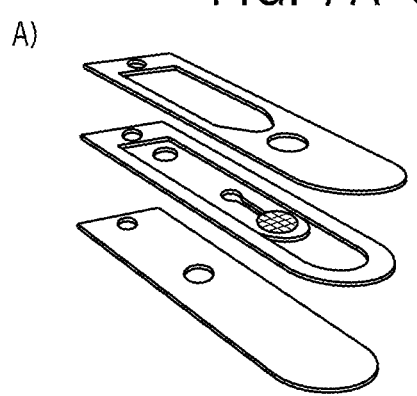
B)
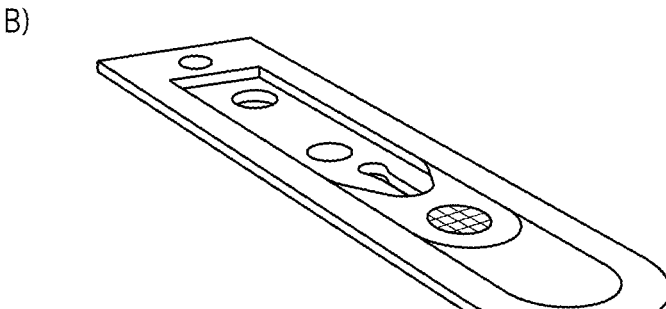
C)
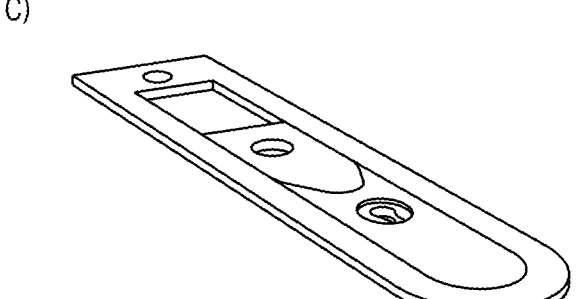

FIG. 8 A-C
A)
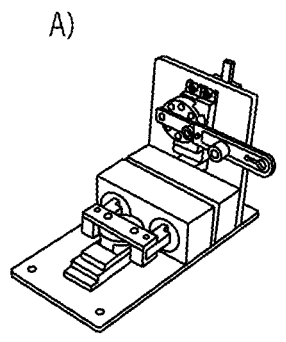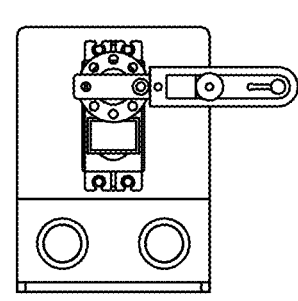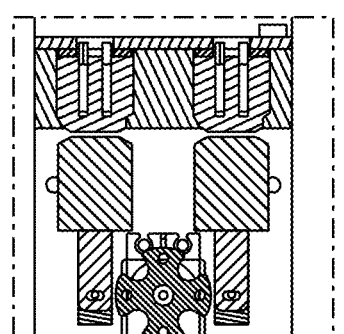
B)
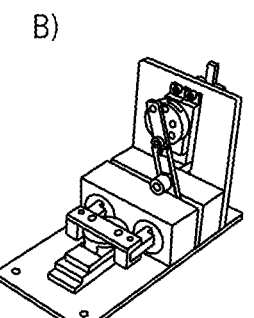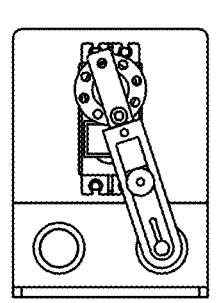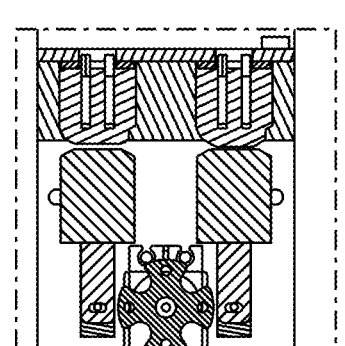
C)
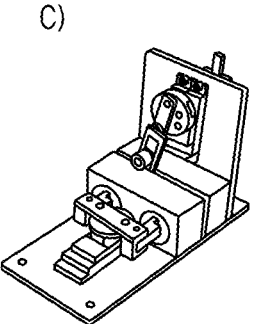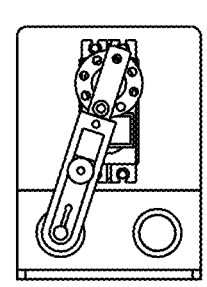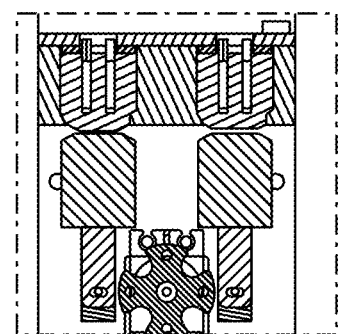

FIG. 11 A-C
A)
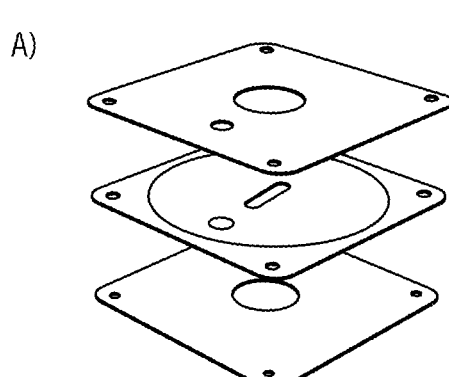
B)
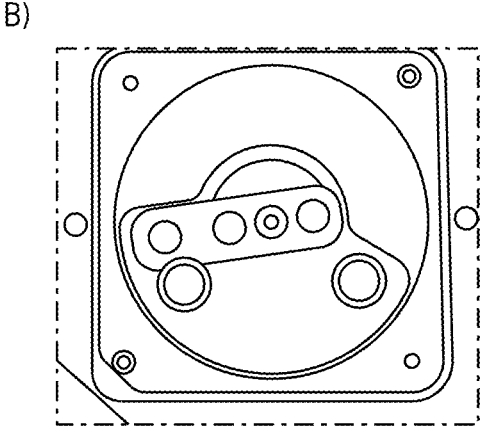
C)
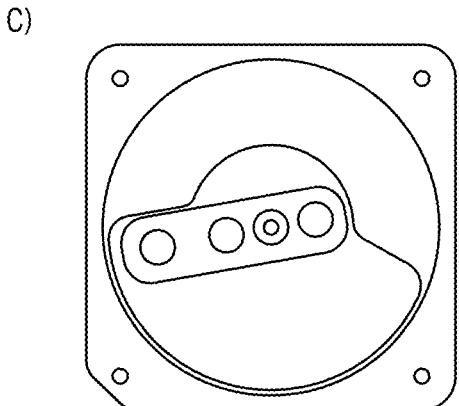

FIG. 12 A-C
A)
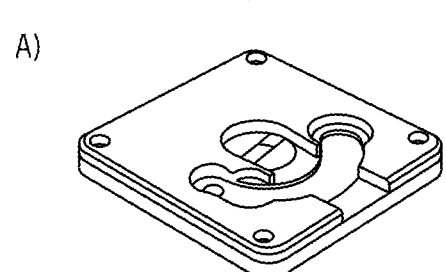
B)
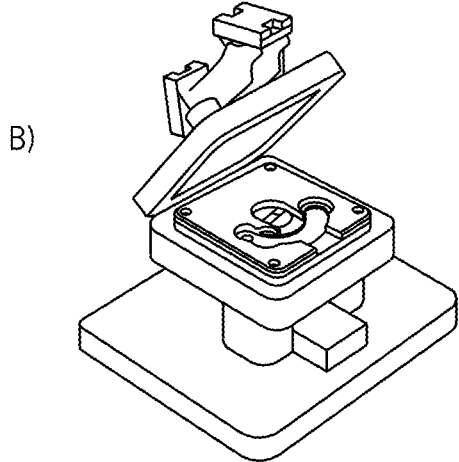
C)
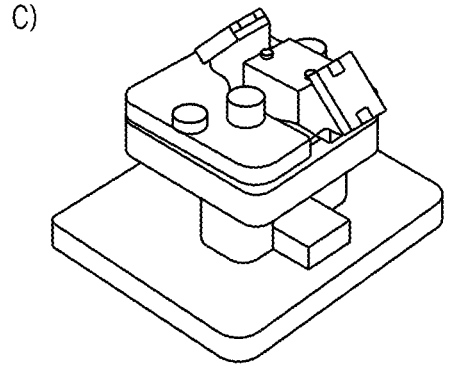

FIG. 14 A-C
A)
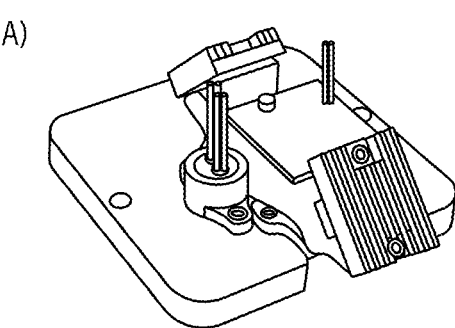
B)
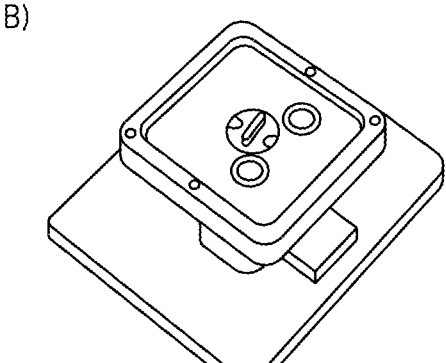
C)
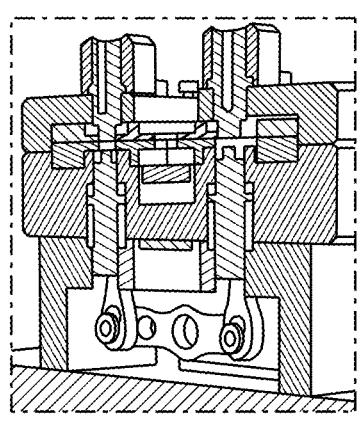

FIG. 14 D-F
D)
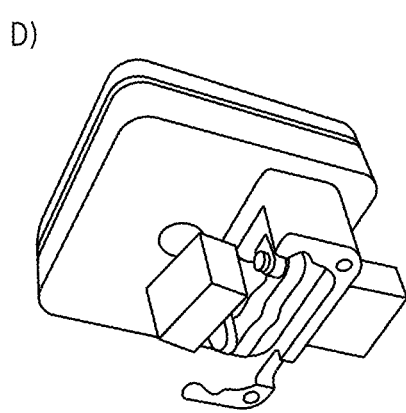
E)
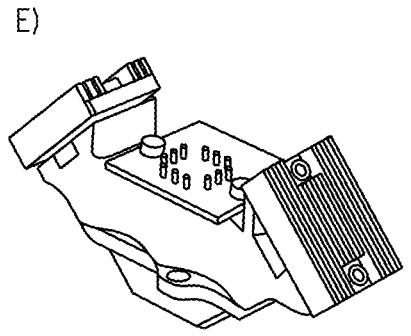
F)
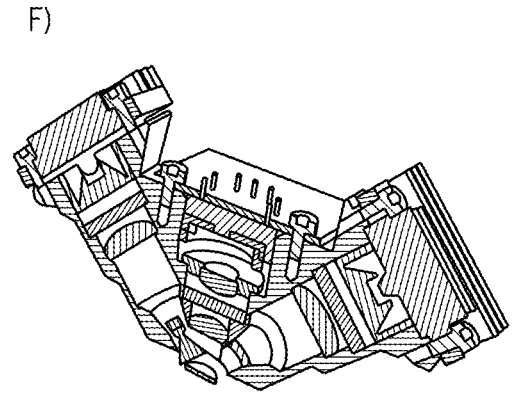

FIG. 15 A-D
A)
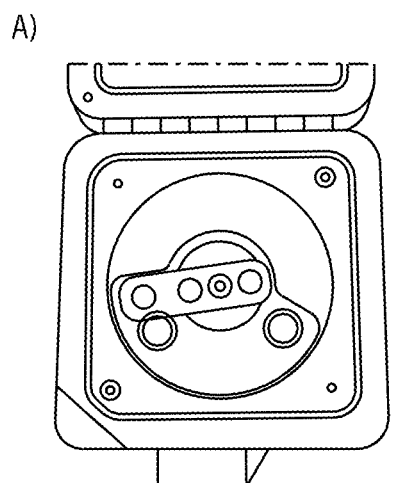
B)
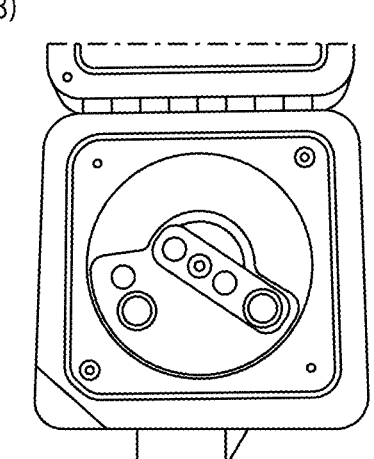
C)
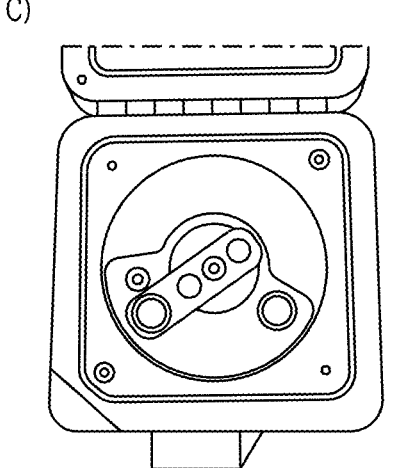
D)
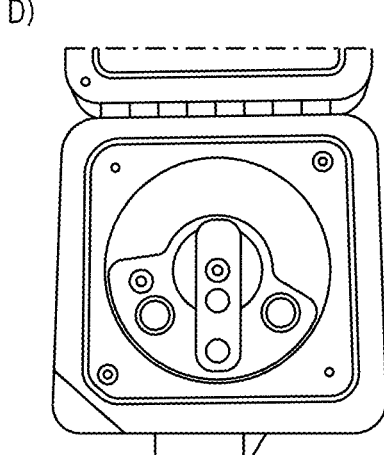

FIG. 16A-B
A)
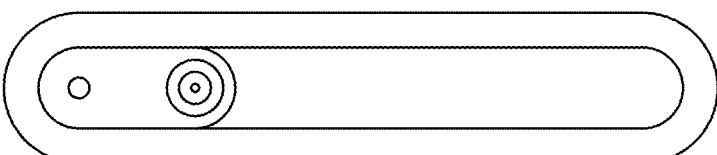
B)
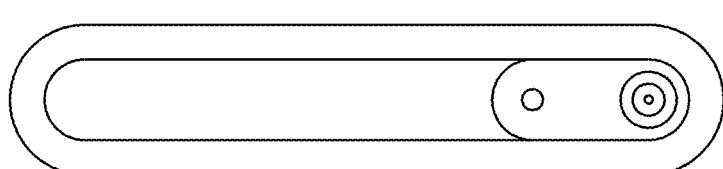

FIG. 17A-B
A)
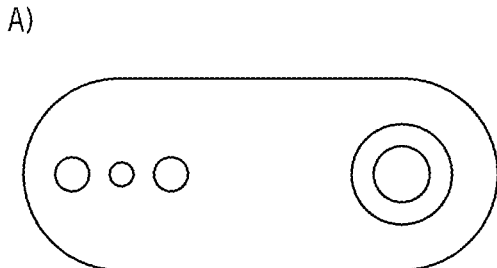
B)
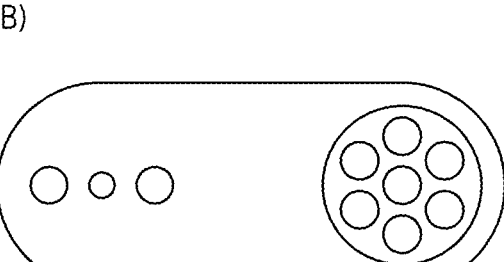

FIG. 18 A-C
A)
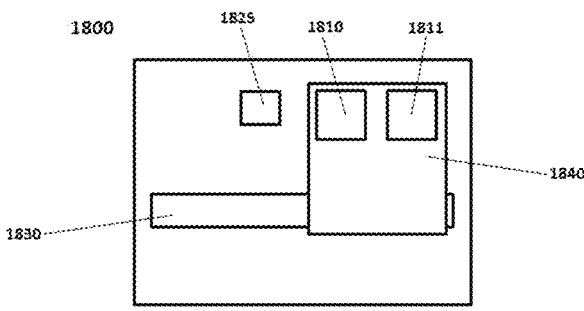
B)
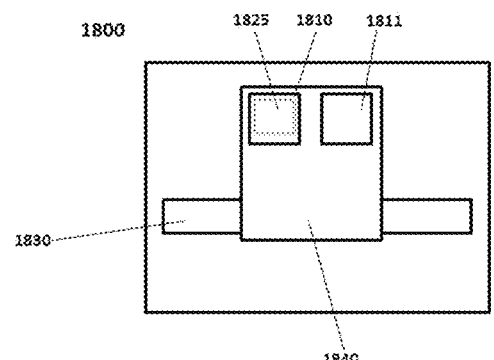
C)
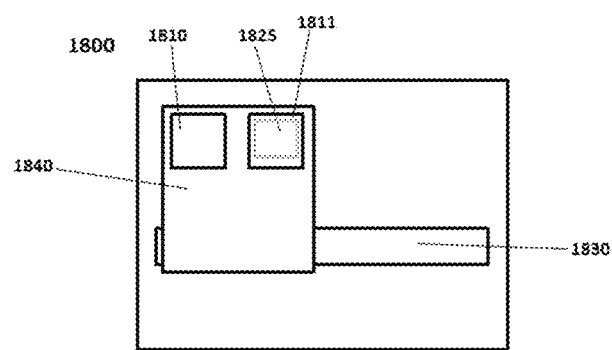

FIG. 19 A-B
A)
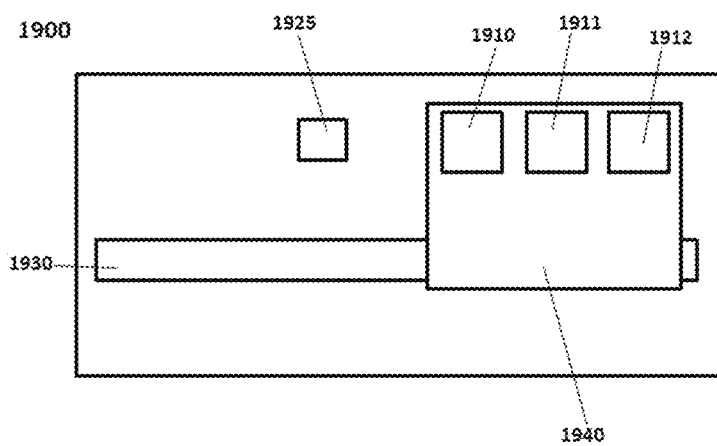
B)
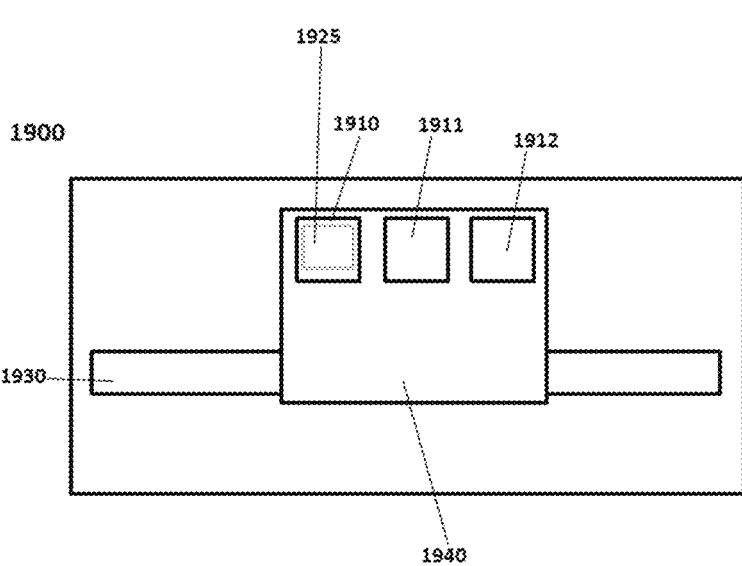

FIG. 19 C-D
C)
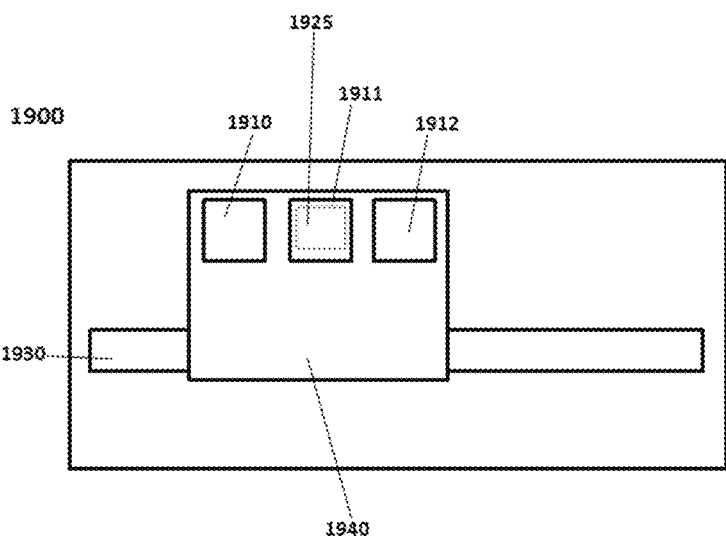
D)
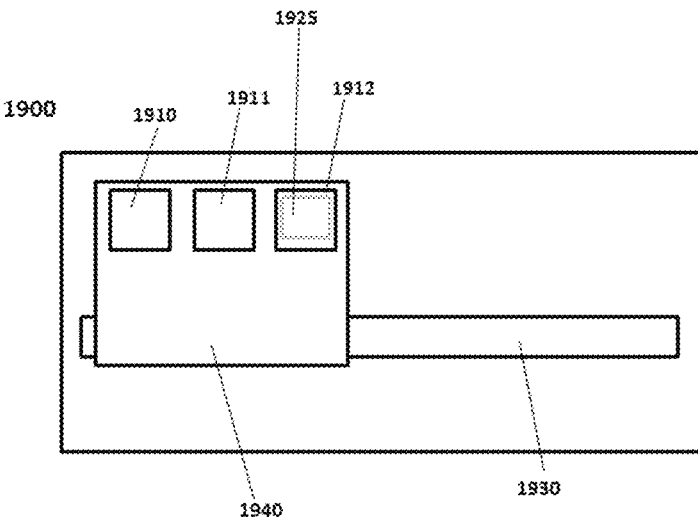

2000

2001

2002

2003

2004

2000

2068

FIG. 21 A-B
A)
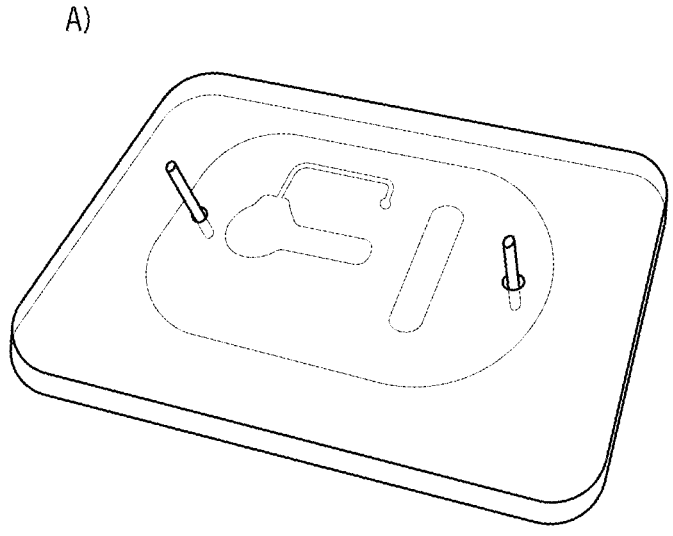
B)
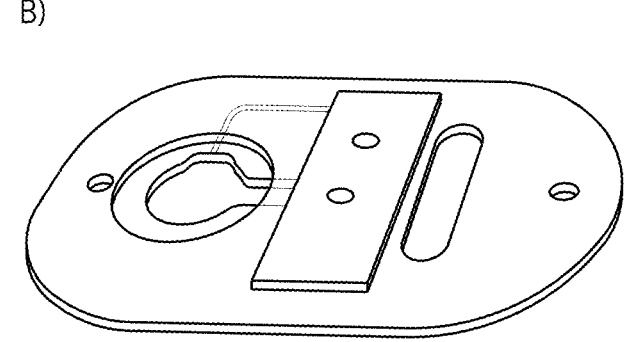

FIG. 21C-D
C)
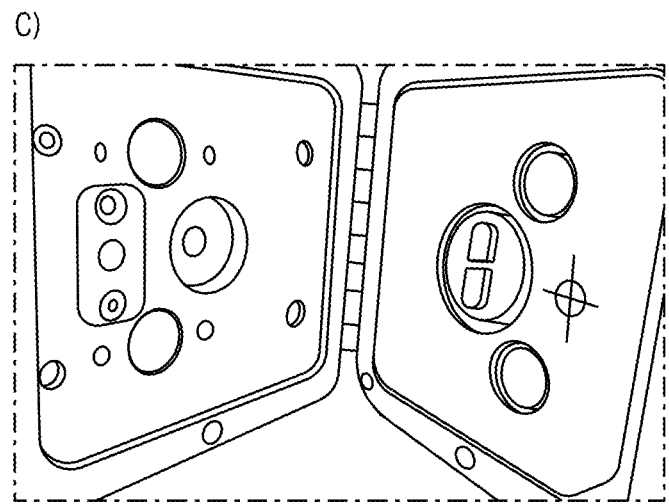
D)
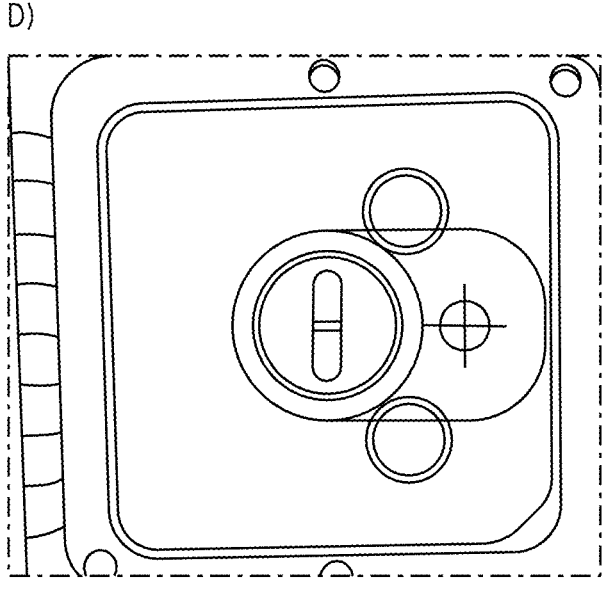

FIG. 21E-F
E)
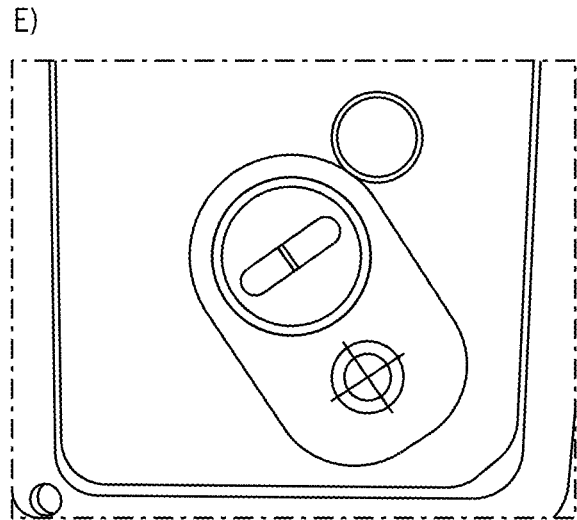
F)
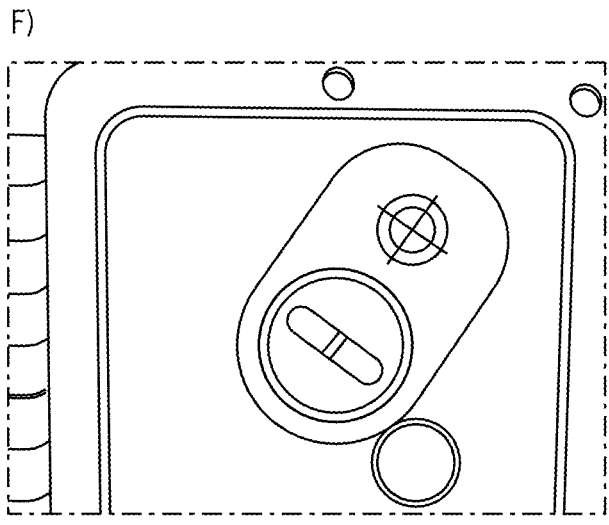

DEVICES AND METHODS FOR RAPID SAMPLE PROCESSING AND ANALYSIS

CROSS-REFERENCE TO RELATED APPLICATION

The present application is a continuation of U.S. patent application Ser. No. 16/615,630, filed Nov. 21, 2019, which is a 371 of International Application No. PCT/US2018/034443, filed May 24, 2018, which claims priority to U.S. Provisional Patent Application Ser. No. 62/510,503 filed May 24, 2017, which is herein incorporated by reference in its entirety.

FIELD

Provided herein are devices and methods for the rapid processing and analysis of samples. In particular, a small-volume sample (e.g., nucleic acid sample) is exposed to (e.g., contacted with) different temperature zones within a device to process (e.g., amplify) and/or analyze (e.g., quantitate) the sample in an assay.

BACKGROUND

Nucleic acid testing provides a method for the detection and diagnosis of infectious diseases among many other uses. The most widely practiced and most reliable methods of nucleic acid testing employ polymerase chain reaction (PCR). A limitation of PCR is that it requires an hour or more to cycle the reaction solution through multiple temperatures, which can differ by 30° C. or more. Quantitative or real-time PCR (qPCR or RT-PCR) takes even longer because fluorescence readings must be taken during or between each thermal cycle. The long processing time and electrical energy required to perform qPCR keep it from being used in many situations where a diagnosis must be made quickly and accurately.

A typical qPCR protocol performs 30-50 cycles of heating the test solution to 95° C., then cooling to 60° C., followed by fluorescence readings. In typical thermal cyclers, the heating and cooling steps are done in plastic tubes with a thermal electric cooler (TEC), which pumps heat in and out of the test solution through the walls of the tube. Such thermal cyclers introduce inefficiencies into the PCR procedures.

SUMMARY

Provided herein are devices and methods for the rapid processing and analysis of samples. In particular, a small-volume sample (e.g., nucleic acid sample) is exposed to (e.g., contacted with) different temperature zones within a device to process (e.g., amplify) and/or analyze (e.g., quantitate) the sample in an assay.

In some embodiments, provided herein are devices comprising: a sample container, a first temperature zone, a second temperature zone, and a shuttling mechanism; wherein the shuttling mechanism physically moves the sample container between the first and second temperature zones. In some embodiments, provided herein are devices comprising: a sample container, a first temperature zone, a second temperature zone, and a shuttling mechanism; wherein a shuttling mechanism physically moves the first and second temperature zones to contact the sample container. In some embodiments, the first and second temperature zones each comprise temperature regulators (e.g., heaters) that the sample container is brought into contact with (or close proximity to (e.g., <5 mm, <4 mm, <3 mm, <2 mm, <1 mm, <0.9 mm, <0.8 mm, <0.7 mm, <0.6 mm, <0.5 mm, <0.4 mm, <0.3 mm, <0.2 mm, <0.1 mm)) when the shuttling mechanism physically moves the sample container into the first and second temperature zones (or moves physically moves the temperature zones to the sample container). In some embodiments, a temperature regulator maintains a fixed temperature within a temperature zone. In some embodiments, temperature regulators are any component that is configured to maintain a constant or near constant temperature (e.g., <10% fluctuation, <5% fluctuation, <2% fluctuation, <1% fluctuation, <0.5% fluctuation, <0.2% fluctuation, <0.1% fluctuation) during use (e.g., when in contact with a sample container, when adjacent to a sample container, in the absence of a sample container, etc.). In some embodiments, devices further comprise a detection zone, wherein the shuttling mechanism physically moves the sample container between the first temperature zone, the second temperature zone, and the detection zone. In some embodiments, one or both of the temperature zones is also a detection zone. In some embodiments, devices further comprise a detection zone, wherein the shuttling mechanism physically moves the first temperature zone, the second temperature zone, and the detection zone to contact the sample. In some embodiments, the detection zone comprises a fluorimeter or image sensor. In some embodiments, the shuttling mechanism comprises a servo. In some embodiments, the shuttling mechanism comprises a stepper motor. In some embodiments, the shuttling mechanism comprises a DC motor and position sensor. In some embodiments, the sample container comprises a well capable of containing a liquid sample. In some embodiments, the sample container comprises a porous material capable of absorbing a liquid sample. In some embodiments, the sample container comprises a channel capable of filling by capillary forces. In some embodiments, provided herein are methods of processing a sample (e.g., a sample comprising a target nucleic acid), comprising: (a) placing a sample in the sample container of the device described herein; and (b) allowing the sample container to be exposed to (e.g., contacted with) the first and second temperature zones for pre-determined times.

In some embodiments, provided herein are devices comprising: a sample container, a first temperature regulator (e.g., heater), a second temperature regulator (e.g., heater), a detector, and a shuttling mechanism (e.g., motor, servo, etc.); wherein the shuttling mechanism (e.g., motor, servo, etc.) physically moves the sample container between first temperature regulator (e.g., heater), the second temperature regulator (e.g., heater), and the image sensor. In some embodiments, provided herein are devices comprising: a sample container, a first temperature regulator (e.g., heater), a second temperature regulator (e.g., heater), a detector, and a shuttling mechanism (e.g., motor, servo, etc.); wherein the shuttling mechanism (e.g., motor, servo, etc.) physically moves the first temperature regulator (e.g., heater), the second temperature regulator (e.g., heater), and the image sensor. In some embodiments, devices further comprise a controller that directs the shuttling mechanism (e.g., motor, servo, etc.). In some embodiments, the detector is an image sensor or fluorometer. In some embodiments, provided herein are methods of processing a sample (e.g., a sample comprising a target nucleic acid), comprising: (a) placing a sample in the sample container of a device described herein; and (b) allowing the sample container to be shuttled between the first temperature regulator (e.g., heater), the second temperature regulator (e.g., heater), and the detector, according to a predetermined cycle; wherein the sample container is maintained at the first temperature regulator (e.g., heater) for sufficient time to bring the sample to the temperature of the first temperature regulator (e.g., heater), wherein the sample container is maintained at the second temperature regulator (e.g., heater) for sufficient time to bring the sample to the temperature of the second temperature regulator (e.g., heater), wherein a characteristic of the sample and/or sample container is obtained in the detector. In some embodiments, provided herein are methods of processing a sample (e.g., a sample comprising a target nucleic acid), comprising: (a) placing a sample in the sample container of a device described herein; and (b) allowing the first temperature regulator (e.g., heater), the second temperature regulator (e.g., heater), and the detector to be shuttled in and out of contact/proximity with the sample container according to a predetermined cycle; wherein the sample container is maintained at the first temperature regulator (e.g., heater) for sufficient time to bring the sample to the temperature of the first temperature regulator (e.g., heater), wherein the sample container is maintained at the second temperature regulator (e.g., heater) for sufficient time to bring the sample to the temperature of the second temperature regulator (e.g., heater), wherein a characteristic of the sample and/or sample container is obtained in the detector.

In some embodiments, provided herein are devices comprising: (a) a sample holder; (b) a sample container located on the sample holder; (c) first and second regulators (e.g., heaters) in opposing orientations thereby creating a gap between the first and second regulators (e.g., heaters); (d) third and fourth regulators (e.g., heaters) in opposing orientations thereby creating a gap between the third and fourth regulators (e.g., heaters); and (e) a shuttling mechanism (e.g., servo, motor, etc.) that physically device moves the sample holder between positions in which the sample container resides (i) within the gap between the first and second regulators (e.g., heaters) and (ii) within the gap between the third and fourth regulators (e.g., heaters). In some embodiments, the shuttling mechanism (e.g., servo, motor, etc.) moves the sample holder. In some embodiments, the shuttling mechanism (e.g., servo, motor, etc.) moves the heat regulators (and gaps therebetween). In some embodiments, devices further comprise a controller that directs the shuttling mechanism (e.g., servo, motor, etc.). In some embodiments, provided herein are methods of processing a sample (e.g., a sample comprising a target nucleic acid), comprising: (a) placing a sample in the sample container of the device of a device herein; and (b) allowing the device to be shuttled between configurations in which the sample container is (i) within the gap between the first and second regulators (e.g., heaters) and (ii) within the gap between the third and fourth regulators (e.g., heaters), according to a predetermined schedule; wherein the sample container is maintained at the gap between the first and second regulators (e.g., heaters) for sufficient time to bring the sample to the temperature of the gap between the first and second regulators (e.g., heaters), and wherein the sample container is maintained at the gap between the third and fourth regulators (e.g., heaters) for sufficient time to bring the sample to the temperature of the gap between the third and fourth temperature regulators (e.g., heaters). In some embodiments, the shuttling mechanism (e.g., servo, motor, etc.) moves the sample holder. In some embodiments, the shuttling mechanism (e.g., servo, motor, etc.) moves the heat regulators (and gaps therebetween).

In some embodiments, provided herein are devices comprising: (a) a sample holder; (b) a sample container located on the sample holder; (c) a detector; (d) first and second regulators (e.g., heaters) in opposing orientations thereby creating a gap between the first and second regulators (e.g., heaters); (e) third and fourth regulators (e.g., heaters) in opposing orientations thereby creating a gap between the third and fourth regulators (e.g., heaters); and (f) a shuttling mechanism (e.g., servo, motor, etc.) that physically orients the device into positions in which the sample container resides (i) within the gap between the first and second regulators (e.g., heaters), (ii) within the gap between the third and fourth regulators (e.g., heaters), and (iii) adjacent to the detector. In some embodiments, the shuttling mechanism (e.g., servo, motor, etc.) moves the sample holder. In some embodiments, the shuttling mechanism (e.g., servo, motor, etc.) moves the heat regulators (and gaps therebetween) and detector. In some embodiments, devices further comprise a controller that directs the shuttling mechanism (e.g., servo, motor, etc.). In some embodiments, the detector is a fluorimeter or image sensor. In some embodiments, provided herein are methods of processing a sample (e.g., a sample comprising a target nucleic acid), comprising: (a) placing a sample in the sample container of the device described herein; and (b) allowing the device to be shuttled between configurations in which the sample container is adjacent to (i) the first and second temperature regulators (e.g., heaters), (ii) the third and fourth temperature regulators (e.g., heaters), and (iii) the detector, according to a predetermined cycle; wherein the sample container is maintained at the gap between the first and second temperature regulators (e.g., heaters) for sufficient time to bring the sample to the temperature of the gap between the first and second temperature regulators (e.g., heaters), wherein the sample container is maintained at the gap between the third and fourth temperature regulators (e.g., heaters) for sufficient time to bring the sample to the temperature of the gap between the third and fourth temperature regulators (e.g., heaters), and wherein a characteristic of the sample and/or sample container is obtained in the detector. In some embodiments, the characteristic is fluorescence intensity. In some embodiments, the shuttling mechanism (e.g., servo, motor, etc.) moves the sample holder. In some embodiments, the shuttling mechanism (e.g., servo, motor, etc.) moves the heat regulators (and gaps therebetween) and detector. In some embodiments, the sample is cycled through the first and second temperature regulators (e.g., heaters), the third and fourth temperature regulators (e.g., heaters), and the detector for 2 or more cycles (e.g., 5, 10, 15, 20, 25, 30, or more cycles).

In some embodiments, provided herein are sample holder devices comprising multiple thin layers, each thin layer having a thickness of 1 mm of less (e.g., 10 µm, 20 µm, 30 µm, 40 µm, 50 µm, 60 µm, 70 µm, 80 µm, 90 µm, 100 µm, 125 µm, 150 µm, 175 µm, 200 µm, 250 µm, 300 µm, 400 µm, 500 µm, 600 µm, 700 µm, 800 µm, 900 µm, 1 mm, or ranges therebetween), the multiple thin layers adhered together to form a card comprising a sample container; wherein a central thin layer comprises a sample containment cutout that forms a sample container when front and rear thin layers are applied to the central layer to form the assembled card; wherein the front thin layer comprises a transparent window that sits adjacent to the containment cutout when the front and central layers are adhered together to form the assembled card; and wherein the assembled card comprises an engagement element for connecting the sample holder device to an instrument. In some embodiments, the entire front thin layer is transparent. In some embodiments, the engagement element comprises a slot cutout in one or both of the front and rear thin layers. In some embodiments, the engagement element comprises a slot cutout in the front, central, and rear thin layers. In some embodiments, devices further comprise a port cutout in the front or rear thin layer, and a port channel in the central layer, wherein the port cutout and port channel align in the assembled card to form a port for adding liquid reagents to the sample container. In some embodiments, a port closure element, wherein when the port closure element is applied over the port cutout on the assembled card, the sample container is sealed. In some embodiments, a vent cutout in the front or rear thin layer, and a vent channel in the central layer, wherein the vent cutout and vent channel align in the assembled card to form a vent for releasing air from the sample container when liquid reagents are added to the sample container via the port. In some embodiments, devices further comprise a vent closure element, wherein when the vent closure element is applied over the vent cutout on the assembled card, the sample container is scaled. In some embodiments, each of the thin layers comprises identical peripheral cross-sections. In some embodiments, one or more support layers adhered to the front and/or rear thin layers. In some embodiments, the support layers are not thin layers (e.g., of greater thickness than the thin layers of the device). In some embodiments, the support layers comprise identical peripheral cross-sections to the multiple thin layers. In some embodiments, support layers comprise cutouts to provide access to the transparent window, engagement element, and sample container when the thin layers and the support layers are assembled into the card. In some embodiments, devices further comprise assay reagents within the sample container. In some embodiments, the assay reagents comprise polymerase chain reaction (PCR) reagents. In some embodiments, the assay reagents are dried onto an interior surface of the sample container.

In some embodiments, provided herein are systems comprising: (a) a sample holder device described herein; and (b) an instrument comprising: (i) a first temperature zone; (ii) a second temperature zone; (iii) a detection zone; and (iv) a shuttling mechanism; wherein the shuttling mechanism is configured for attachment to the engagement element of the sample holder device, and when activated, is configured to shuttle the sample container between the first temperature zone, the second temperature zone, and the detection zone according to a predetermined cycle. In some embodiments, the detection zone comprises a fluorimeter or image sensor. In some embodiments, the shuttling mechanism comprises a motor or servo. In some embodiments, the first and second temperature zones each comprise a heater that the sample container is brought into contact with or proximity to when the shuttling mechanism physically moves the sample container into the first and second temperature zones, respectively. In some embodiments, the first and second temperature zones each comprise two opposing heaters that the sample container is brought between the two opposing heaters when the shuttling mechanism physically moves the sample container into the first and second temperature zones, respectively. In some embodiments, one or both of the heaters in a pair of two opposing heaters is movable, and wherein the heaters are configured to enclose upon the sample container when it enters the temperature zone and to release the sample container as it exits the temperature zone.

In some embodiments, provided herein is the use of the devices and methods described herein for the amplification, detection, and/or quantification of target nucleic acids. In some embodiments, the use of the devices herein to perform PCR, qPCR, RT-PCR, RT-qPCR, etc. is provided.

In some embodiments methods are provided for performing PCR, qPCR, RT-PCR, RT-qPCR, etc. using the devices described herein. In some embodiments, reagents, temperatures, times, cycles, etc., and any method steps or device components are provided according to the details described herein and understood in the field.

BRIEF DESCRIPTION OF THE DRAWINGS

FIG. 3A-B. Schematic depicting an exemplary device 300 comprising a sample container 325 on a sample disc 320; a shuttle drive motor 330 oscillates the sample disc between two positions, resulting in the sample container 325 moving between (A) a first temperature zone 310 and (B) a second temperature zone 311.

FIG. 4A-C. Schematic depicting an exemplary device 400 comprising a sample container 425 on a sample disc 420; a shuttle drive motor 430 oscillates the sample disc between three positions, resulting in the sample container 425 moving between (A) a first temperature zone 410, (B) a detection zone 411, and (C) a second temperature zone 412.

FIG. 5A-C. Schematic depicting an exemplary device 500 comprising a sample container 525 on a sample arm 520; a shuttle drive motor 530 slides the sample arm between three positions, resulting in the sample container 525 moving between (A) a first temperature zone 510, (B) a detection zone 511, and (C) a second temperature zone 512.

FIG. 6A-B. (A) Magnified image of glass fiber material of an exemplary sample container (e.g., porous media container (PMC)). (B) Drawing (top view) of a sample arm (blade configuration), PMC (hatched circle), and holes used to attach the blade to a shuttle mechanism.

FIG. 7A-C. Drawings of an exemplary cartridge for use in certain embodiments herein. (A) Drawing of a three-layer cassette, depicting a top film, blade and PMC, and bottom film. In some embodiments, a transfer adhesive bonds the films together to contain the blade and PMC. (B) Assembled cassette with PMC positioned under a port through the top film through which a sample (e.g., PCR reagents, target nucleic acids, etc.) are added. (C) Assembled cassette in forward position with PMC is covered on both sides by transparent, vapor barrier film. Port is sealed to reduce vapor loss during cycling.

FIG. 8A-C. Drawings of an exemplary thermal cycling device, comprising a sample cassette as depicted in FIG. 7, depicted in three different views: perspective (left); front view of cassette, shuttle drive, and heaters (middle); and top-section view of servo and heaters (right). (A) The cassette is mounted onto the arm, which is driven by the shuttle servo on the rear, vertical plate. When the cassette moves, the front heaters are both pulled back creating a gap with the back heaters. (B) The shuttle servo moves the PMC in the slide into the first temperature zone (e.g., between a first set of heaters (e.g., 95° C. heaters)). The heater servo, on the horizontal plate, moves the front heater to contact the cassette and press it up against the back heater. (C) The servo unclamps the cassette, which then is moved to the second temperature zone (e.g., between a second set of heaters (e.g., 60° C. heaters)) by the shuttle servo. Once in position between the second heaters, the heater servo clamps down.

FIG. 9A-B. (A) Image of the exemplary device depicted in the drawings of FIG. 8 interfaced with controllers. (B) Temperature response measured with thermocouple inserted between two 0.25 mm thick filters in the device depicted in (A). Time to heat from 57° C. to 97° C. is 3.6 s. Time to cool from 97° C. to 57° C. is 4.1 s. The time constant is approximately 1 s.

FIG. 11A-C. (A) Drawing of an exemplary cassette comprising a disc that holds the PMC and is driven mechanically through engagement of a slot. (A) Drawing of a three-layer cassette, depicting a top film, blade and PMC, and bottom film. (B) Image of an exemplary cassette comprising a semi-rectangular sample arm that rotates through the cassette to move the PMC between the temperature zones; 360° rotation is possible. (C) Drawing of an exemplary cassette comprising a barrier region above the rotatable area of the sample arm; the barrier provides stops to better couple the blade to shuttle magnets.

FIG. 12A-C. Drawings of an exemplary device comprising a disc cassette, such as those depicted in FIGS. 10-11. (A) Rigid cartridge containing the disc cassette. (B) Cartridge is contained within the exemplary device. (C) Cover of device is closed and held in place, for example, with thumb screws.

FIG. 14A-F. Drawing depicting exemplary device subsystems. (A) Top cover, hinged in the back to open, comprises two stationary heaters and fluorimeter. (B) Base comprises two heaters that are moved up and down by the servo. The disc holding the PMC is rotated by the central hub which is driven by a servo. (C) Section view with cover closed depicts the mechanism that moves the bottom heaters up and down. (D) Bottom perspective view depicting shuttle servo, heater linkages, and servo. (E) Fluorimeter assembly with detector board and two LEDs with heat sinks. (F) Section view of fluorimeter depicting LEDs, lenses, interference filters, and detector.

FIG. 15A-D. Images of an exemplary device in the steps of a PCR cycle. (A) When the cartridge is loaded, the disc is positioned so the PMC is under the fill port. (B) Rotated to align PMC with the high temperature heater. (C) The servo rotates the disc and the PMC to the low temperature heater. (D) The servo moves the blade and PMC to the fluorimeter read position.

FIG. 16A-B. Drawings of a portion of an exemplary cassette in which the sample holder comprising a sample container slides linearly between at least first (A) and second (B) positions on the cassette.

FIG. 17A-B. Drawings of exemplary alterations to a sample holder. (A) Material immediately surrounding the sample container comprises a heat conducting material, while the further surrounding material is a cheaper and/or less conductive material. (B) Multiple sample containers on a single sample holder.

FIG. 18A-C. Schematic depicting an exemplary device 1800 comprising (A) a sample container 1825; a first temperature zone 1810; a second temperature zone 1811; a zone holder 1840; a shuttle mechanism 1830 slides the zone holder 1840, resulting in alignment of the sample container 1825 with (B) the first temperature zone 1810 and (C) the second temperature zone 1811.

FIG. 19A-D. Schematic depicting an exemplary device 1900 comprising (A) a sample container 1925; a first temperature zone 1910; a second temperature zone 1911; a detection zone 1912; a zone holder 1940; a shuttle mechanism 1930 slides the zone holder 1940, resulting in alignment of the sample container 1925 with (B) the first temperature zone 1910, (C) the second temperature zone 1911, and (C) the detector 1912.

FIG. 21A-F. Images of exemplary sample holder: (A) layers assembled on fixture with two assembly dowels through assembly guides; (B) port/vent cover (tape) adhered to support layer; (C) device without sample holder, device is opened up to revel the shuttling mechanism and rear heaters (right) and detector and front heaters (left); (D) sample holder attached to device, aligned in 'read' position; (E) sample holder attached to device, aligned with a first temperature zone; and (F) sample holder attached to device, aligned with a second temperature zone.

DEFINITIONS

Figure 1A:
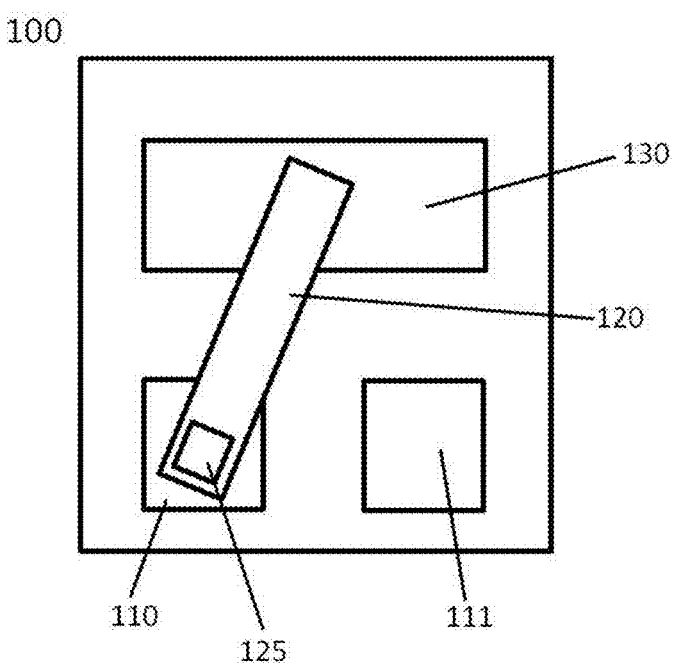
FIG. 1A-B. Schematic depicting an exemplary device 100 comprising a sample container 125 on a sample arm 120; a shuttle drive motor 130 oscillates the sample arm between two positions, resulting in the sample container 125 moving between (A) a first temperature zone 110 and (B) a second temperature zone 111.

To facilitate an understanding of the present technology, a number of terms and phrases are defined below. Additional definitions are set forth throughout the detailed description.

As used herein, "a" or "an" or "the" can mean one or more than one. For example, "a" widget can mean one widget or a plurality of widgets.

As used herein, the terms "subject" and "patient" refer to any animal, such as a dog, cat, bird, livestock, and particularly a mammal, preferably a human.

As used herein, the term "comprise" and linguistic variations thereof denote the presence of recited feature(s), element(s), method step(s), etc. without the exclusion of the presence of additional feature(s), element(s), method step(s), etc. Conversely, the term "consisting of" and linguistic variations thereof, denotes the presence of recited feature(s), element(s), method step(s), etc. and excludes any unrecited feature(s), element(s), method step(s), etc., except for ordinarily-associated impurities. The phrase "consisting essentially of" denotes the recited feature(s), element(s), method step(s), etc. and any additional feature(s), element(s), method step(s), etc. that do not materially affect the basic nature of the composition, system, or method. Many embodiments herein are described using open "comprising" language. Such embodiments encompass multiple closed "consisting of" and/or "consisting essentially of" embodiments, which may alternatively be claimed or described using such language.

As used herein, the term "sample" and "specimen" are used interchangeably, and in the broadest senses. In one sense, sample is meant to include a specimen or culture obtained from any source, as well as biological and environmental samples. Biological samples may be obtained from animals (including humans) and encompass fluids, solids, tissues, and gases. Biological samples include blood products, such as plasma, serum, stool, urine, and the like. Environmental samples include environmental material such as surface matter, soil, mud, sludge, biofilms, water, and industrial samples. Such examples are not however to be construed as limiting the sample types applicable to the present invention.

The term "system" as used herein refers to a collection of compositions, devices, articles, materials, etc. grouped together in any suitable manner (e.g., physically associated; in fluid-, electronic-, or data-communication; packaged together; etc.) for a particular purpose.

As used herein, the term "preparing" and linguistic equivalents thereof refers to any steps taken to alter a sample or one or more components thereof, for example, for use in a subsequence analysis or detection step. Exemplary sample preparation steps include, for example, dilution or concentration of a sample, isolation or purification of a sample component, heating or cooling a sample, amplification of a sample component (e.g., nucleic acid), labeling a sample components, etc.

As used herein, the term "analyzing" and linguistic equivalents thereof refers to any steps taken to a characterize a sample or one or more components thereof. Exemplary analysis steps include, for example, quantification of a sample component (e.g., a target nucleic acid), sequencing a sample component, etc.

In some embodiments, sample preparation steps and analysis steps take place simultaneously and/or are repeated in series. For example, in qPCR, nucleic acid amplification and quantification steps are repeated in succession.

DETAILED DESCRIPTION

Provided herein are devices and methods for the rapid processing and analysis of samples. In particular, a small-volume sample (e.g., nucleic acid sample) is exposed to (e.g., contacted with) different temperature zones within a device to process (e.g., amplify) and/or analyze (e.g., quantitate) the sample in an assay.

Embodiments herein overcome the limitations of traditional thermal cyclers and PCR protocols by eliminating bulky sample containers (e.g., plastic tubes) and thermoelectric coolers (TECs) from the devices and methods herein. In some embodiments, a small volume of sample or test solution (e.g., comprising a target nucleic acid and other reagents (e.g., amplification reagents, detection reagents, etc.)) is maintained in a position on the device (e.g., held in place by capillary forces (e.g., between two surfaces (e.g., thin plastic films), within a container, in a porous media container (PMC), etc.), and is shuttled between two or more fixed-position temperature zones (e.g., temperature regulators (e.g., heaters)). In some embodiments, in addition to being shuttled between the fixed-position temperature zones, the sample or test solution is shuttled to a detection zone (e.g., a fluorescence reader) for periodic analysis. In some embodiments, a cycle comprises shuttling of the sample container through two or more temperature zones and a detection zone. In some embodiments, shuttling the sample container between zones comprises moving the sample container (and/or sample holder) with respect to the rest of the device (and/or with respect to the zones (e.g., temperature zone, detection zone, etc.)). In some embodiments, the shuttling the sample container between zones comprises moving the zones (e.g., temperature zone, detection zone, etc.) with respect to the rest of the device (and/or with respect to the sample container). In some embodiments, methods comprise two or more cycles (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more, or ranges therein (e.g., 10-35 cycles) through a series of zones (e.g., one cycle equals first temperature zone, second temperature zone, and detection zone).

In some embodiments, the sample or test solution is contained within the device using a relatively small mass of materials for containment (e.g., containment materials are less than 25% (e.g., 20%, 15%, 10%, 9%, 8%, 7%, 6%, 5%, 4%, 3%, 2%, 1%, or ranges therebetween) of the mass of the contained test solution). In some embodiments, the test solution fills at least 50% (50%, 55%, 60%, 70%, 75%, 80%, 85%, 90%, 95%, 99%, or more, or ranges therebetween) of the available containment volume within a containment zone (e.g., leaving relatively little air in the containment zone to be heated and/cooled). In some embodiments, the only significant masses that change temperature each cycle are the sample or test solution and the containment materials. In some embodiments, the containment zone is an empty chamber or container. In some embodiments, the containment zone comprises a chamber or container comprising containment materials within. In some embodiments, the containment materials comprise a porous media container (PMC). In some embodiments, the containment materials comprise a hydrogel. Hydrogels are materials that absorb solvents (such as water), undergo rapid swelling without discernible dissolution, and maintain three-dimensional networks capable of reversible deformation. Sec, e.g., Park, et al., *Biodegradable Hydrogels for Drug Delivery*, Technomic Pub. Co., Lancaster, Pa. (1993); incorporated by reference in its entirety. Exemplary hydrogels are understood in the field and described in, for example U.S. Pat. No. 6,605,294; incorporated by reference in its entirety. In some embodiments, the containment materials comprise a super absorbent polymer (SAP) and/or superporous hydrogel (SPH), such as those comprising polymers of acrylamide, acrylic acid, salts and esters of acrylic acid including sodium and sulfopropyl acrylates, 2-hydroxyethyl methacrylate, etc. (See, e.g., Omidian et al. Journal of Controlled Release 102 (2005) 3-12; incorporated by reference in its entirety). In some embodiments, the test solution is maintained by capillary forces between two surfaces (e.g., films, membranes, etc. In some embodiments, a container comprises a well (e.g., covered by a lip, film, membrane, etc.).

In some embodiments, a sample container is formed by three layers: (i) a first layer of material forms the back (or bottom) of the container, (ii) a second layer forms the walls of the container and optionally channels to/from the container, and (iii) a third layer forms the front (or top) of the container (FIG. 20).

In some embodiments, the first and third layers are thin films that are applied (e.g., adhered) to the center layer. The rigidity, thermal resistance, vapor barrier, and autofluorescence of the film materials can affect the performance of a device (e.g., shuttling performance, heating performance, detection performance, etc.). Suitable materials for construction of devices are described herein and understood in the field; however, experiments conducted during development of embodiments herein determined that film materials with desirable combinations of characteristics include cyclo olefin polymer (COP; ZEONEX®) cyclo olefin copolymer (COC; TOPAS), at thicknesses of 10-500 µm (e.g., 10 µm, 25 µm, 50 µm, 75 µm, 100 µm, 150 µm, 200 µm, 250 µm, 300 µm, 400 µm, 500 µm, or ranges therebetween).

In some embodiments, the sample container and/or other openings are cuts into the center layer of the device. Suitable techniques for fabricating openings/cuts in the center layer (or other layers) include laser cutting, knife cutting, die cutting, water jet cutting, etc. In some embodiments, holes or slots through the first or third layers provide vents (e.g., for exchange of gases with the container) and/or ports (e.g., for exchange of liquids with the container). In some embodiments, the thickness of the center layer affects the volume of the container. In some embodiments, experiments conducted during development of embodiments herein demonstrated that cutting (laser cutting) of films/layers comprising polycarbonate resulted in high levels of background fluorescence due to residue from melted material around the edge of the cut; the use of, for example, cyclo olefin polymer (COP; ZEONEX®; (e.g., ZF14-188)) eliminated the residual fluorescence. also have desirable properties In some embodiments, the layers (e.g., films) are adhered to one another (e.g., by an adhesive). In some embodiments, a low-fluorescence adhesive is used to bond the first and/or third layers to the center layer. Suitable low-fluorescence adhesives include, but are not limited to 3M™ Silicone Adhesive Transfer Tape 91022, 3M™ Silicone Double Coated Tape 96042, Adhesive Research Silicone Transfer Film ARcare 7876, etc.

In some embodiments, black and/or opaque materials are advantageous for the center layer due to the low levels of autofluorescence produced by such materials and their ability to block autofluorescence from adhesives or other sources. Materials with desirable properties include black polyethylene terephthalate films (PET; CARBON-FEATHER; Kimoto (e.g. 188 X1B))

In some embodiments, in addition to the layers that form the sample container, one or more support layers (e.g., a top/front support layer and a bottom/back support layer) are provided (e.g., adhered to the first and third layers) (FIG. 21A). In some embodiments, because the layers that form the sample contained are very thin, binding them to thicker supporting layers improves handling and manufacturability. In some embodiments, holes are cut through the supporting layers for filling, venting, heat transfer and fluorescence readings. In some embodiments, one or more of the holes through the support layer(s) is covered with an opaque material (e.g., pressure-sensitive adhesive tape (e.g., is 3M Scotch® Super 33+™ Vinyl Electrical Tape)) for operation of the device. In some embodiments, a suitable material for a support layers includes polycarbonate (e.g., clear polycarbonate) or other polymer or non-polymer materials described herein. In some embodiments, a support layer is 0.1 to 4 mm in thickness (e.g., 0.1 mm, 0.15 mm, 0.2 mm, 0.25 mm, 0.3 mm, 0.35 mm, 0.4 mm, 0.45 mm, 0.5 mm, 0.55 mm, 0.6 mm, 0.65 mm, 0.7 mm, 0.75 mm, 0.8 mm, 0.85 mm, 0.9 mm, 0.95 mm, 1 mm, 1.25 mm, 1.5 mm, 1.75 mm, 2 mm, 2.5 mm, 3 mm, 4 mm, or ranges therebetween).

In some embodiments, a container (e.g., well, spot, etc.) containing a sample is shuttled (e.g., physically moved) between multiple distinct temperature zones and/or sample detection zones in/on a device or system. In some embodiments, the sample remains within the container, and the container itself is shuttled between zones in/on the device. In some embodiments, the characteristics/functionalities of the various zones (e.g., temperature) remain constant, and different steps in sample preparation/analysis are performed as the sample (within the container) is moved through the various zones.

In some embodiments, a container (e.g., well, spot, chamber, etc.) containing a sample is maintained in a static position on a device and multiple distinct temperature zones and/or sample detection zones are shuttled (e.g., physically moved) in/on a device or system. In some embodiments, the sample remains within the container, the container remains static, and the zones are shuttled in/on the device. In some embodiments, multiple distinct temperature zones and/or sample detection zones are maintained in a static position on a devic, and a sample container (e.g., well, spot, chamber, etc.) is shuttled (e.g., physically moved) in/on a device or system. In some embodiments, the sample remains within the container, the zones remain static, and the container is shuttled in/on the device. In some embodiments, the characteristics/functionalities of the various zones (e.g., temperature) remain constant, and different steps in sample preparation/analysis are performed as the various zones and the sample container are moved into and out of proximity with each other.

Keeping the sample within the container, and instead shuttling the container and/or zones reduces sample loss, reduces risk of contamination, reduces the time to perform steps, etc. Keeping the characteristics/functionalities of the various zones (e.g., temperature zones) constant and shuttling the sample container between zones (or zones to the container), rather than altering the characteristics/functionalities of the zones, reduces time and cost of performing the steps.

In some embodiments, devices/systems herein comprise one or more sample containers, two or more (e.g., 2, 3, 4, 5, 6, 7, 8, 9, 10, or more, or ranges therebetween) preparation/analysis zones (e.g., temperature zones, image senor, etc.), and a shuttling mechanism to move the sample container between the preparation/analysis zones, for example, in a defined order. In some embodiments, the sample container is in/on a sample holder (e.g., cassette, arm, disc, etc.), and the holder engages the shuttling mechanism to facilitate the movement of the sample container between the preparation/analysis zones. In some embodiments, the preparation/analysis zones, or a component of the device within/upon which the zones reside, engages the shuttling mechanism to facilitate the movement of the preparation/analysis zones into and out of proximity of (e.g., contact with) the sample container.

Unless specified, the devices/systems within the scope herein are not limited by the orientation, shapes, sizes, materials, and/or means of connection of the individual elements of the devices/systems. For example, FIGS. 1-5 provide schematics depicting exemplary embodiments of devices within the scope herein. Embodiments herein are not limited to the configurations in FIGS. 1-5; rather, they depict exemplary configurations which may be altered and/or combined with other details and embodiments described herein.

Figure 1B:
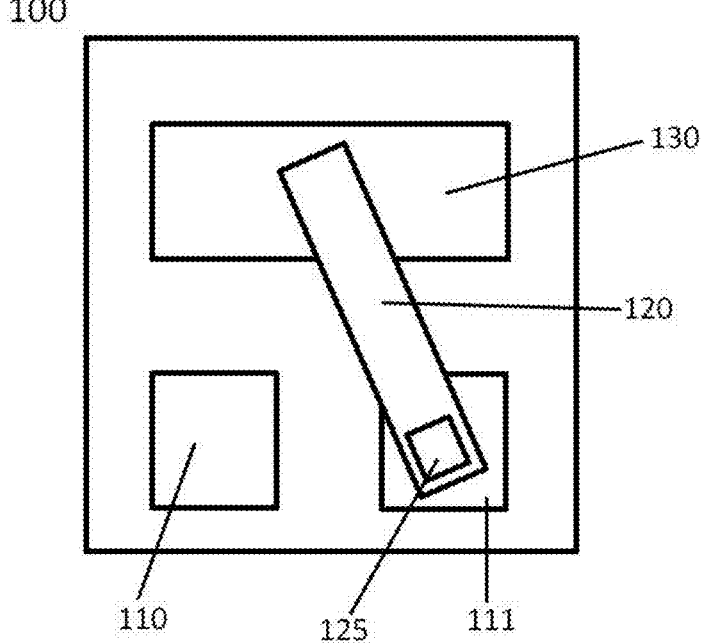

FIG. 1A-B depicts an exemplary device 100 comprising a sample container 125 on a sample arm 120; a shuttle drive motor 130 oscillates the sample arm between two positions, resulting in the sample container 125 moving between (A) a first temperature zone 110 and (B) a second temperature zone 111. In some embodiments, the sample arm 120 is connected to the shuttle drive motor 130, such that the rotation of the shuttle drive motor 130 between defined positions moves the sample container 125 between the first 110 and second 111 temperature zones. The sample container 125 may be any suitable material or arrangement (e.g., well, etc.) for containing a liquid sample. The temperature zones may each comprise one or more heating elements that the sample container is brought into close proximity to (e.g., 5 mm, 4 mm, 3, mm, 2 mm, 1 mm, 0.5 mm, 0.4 mm, 0.2 mm, 0.1 mm, or less, or ranges therebetween) or direct contact with.

Figure 2A:
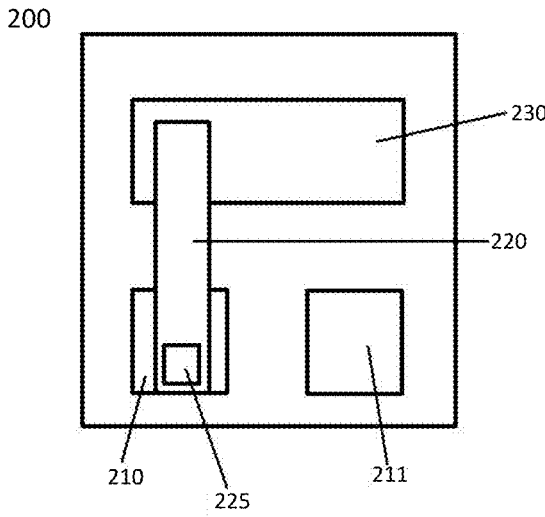
FIG. 2A-B. Schematic depicting an exemplary device 200 comprising a sample container 225 on a sample arm 220; a shuttle drive motor 230 slides the sample arm between two positions, resulting in the sample container 225 moving between (A) a first temperature zone 210 and (B) a second temperature zone 211.
Figure 2B:
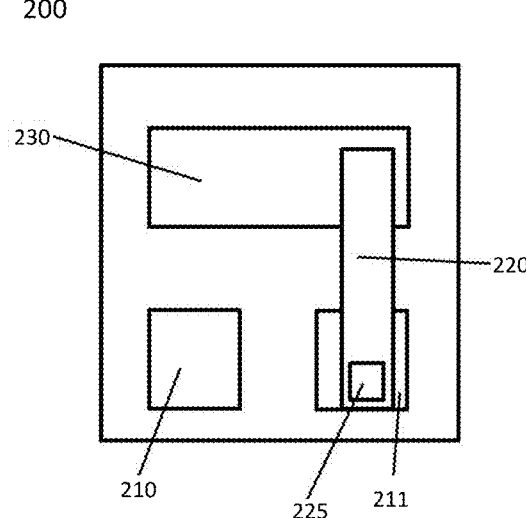

FIG. 2A-B depicts an exemplary device 200 comprising similar components to FIG. 1A-B (e.g., container 225, sample arm 220, shuttle drive motor 230, first temperature zone 210, second temperature zone 211), but with an alternative mechanism for engagement of the sample are 220 by the shuttle drive motor 230. The shuttle drive motor 230 slides the sample arm 220 between two positions, thereby moving the sample container 225 between the first 210 and second 211 temperature zones.

FIG. 3A-B depicts an exemplary device 300 comprising a sample disc 320 in place of the sample arm of FIGS. 1-2. Similar to FIG. 1, rotation of the shuttle drive motor 330 between defined positions moves the sample container 325 between the first 310 and second 311 temperature zones. Alternative means and mechanisms for interaction between the shuttle drive motor, sample holder (e.g., arm or disc), and sample container, other than those depicted in FIGS. 1-3, are within the scope herein.

FIG. 4A-C depicts an exemplary device 400, similar to device 300 of FIG. 3, but with a first temperature zone 410, a detection zone 411, and a second temperature zone 412. The arrangement and/or orientation of these zones is not limiting on the devices herein. The shuttle mechanism 430 moves the sample container 425 between the temperature and detection zones, and is not limited by the order in which the sample container 425 is placed in the various zones. In some embodiments, devices may comprise additional temperature zones, additional detection zones, and/or other zones into which a sample container is placed.

FIG. 5A-C depicts an exemplary device 500 comprising a first temperature zone 510, a detection zone 511, and a second temperature zone 512, similar to FIG. 4, but the sample container 525 resides on a sample arm 520, similar to FIG. 2. The various elements, details, orientations, and arrangements depicted in FIGS. 1-5, and described herein, may be combined in any suitable combinations to provide a device/system for sample preparation and/or analysis.

FIGS. 6-9 and 11-17 depict exemplary devices and elements thereof that find use in embodiments herein. Combination and/or rearrangement of these elements and/or of elements of these devices with other embodiments described herein to provide a suitable device/system for sample preparation and/or analysis is within the scope herein.

FIG. 18A-C depicts an exemplary device 1800 comprising similar components to FIG. 2A-B (e.g., container 1825, shuttle mechanism 1830, first temperature zone 1810, second temperature zone 1811), but with the temperature zones being positioned on a holder 1840 which engages the shuttle mechanism 1830. The shuttle mechanism 1830 slides the holder 1840 (and therefore the temperature zones) between multiple positions, thereby aligning the first 1810 and second 1811 temperature zones with the sample container 1825.

FIG. 19A-D depicts an exemplary device 1900 comprising similar components to FIG. 5A-B (e.g., container 1925, shuttle mechanism 1930, first temperature zone 1910, second temperature zone 1911, detector 1912), but with the temperature zones and detector being positioned on a holder 1940 which engages the shuttle mechanism 1930. The shuttle mechanism 1930 slides the holder 1940 (and therefore the temperature zones) between multiple positions, thereby aligning the first temperature zone 1910, the second temperature zone 1911, and the detector 1912 with the sample container 1925. The various elements, details, orientations, and arrangements depicted in other figures, and described herein, may be combined in any suitable combinations to provide a device/system for sample preparation and/or analysis. The devices/systems herein expose a sample to various conditions (e.g., temperatures) and/or detect various characteristics (e.g., fluorescence) of the sample by physically moving the sample between various preparation/analysis zones (or moving the various preparation/analysis zones into and out of proximity of the sample). The sample is moved between the preparation/analysis zones without removing the sample from the sample container; rather, the sample container itself, with the sample contained within, is moved between the various preparation/analysis zones of the device (or the various preparation/analysis zones are moved into and out of proximity of the sample).

Figure 20A:
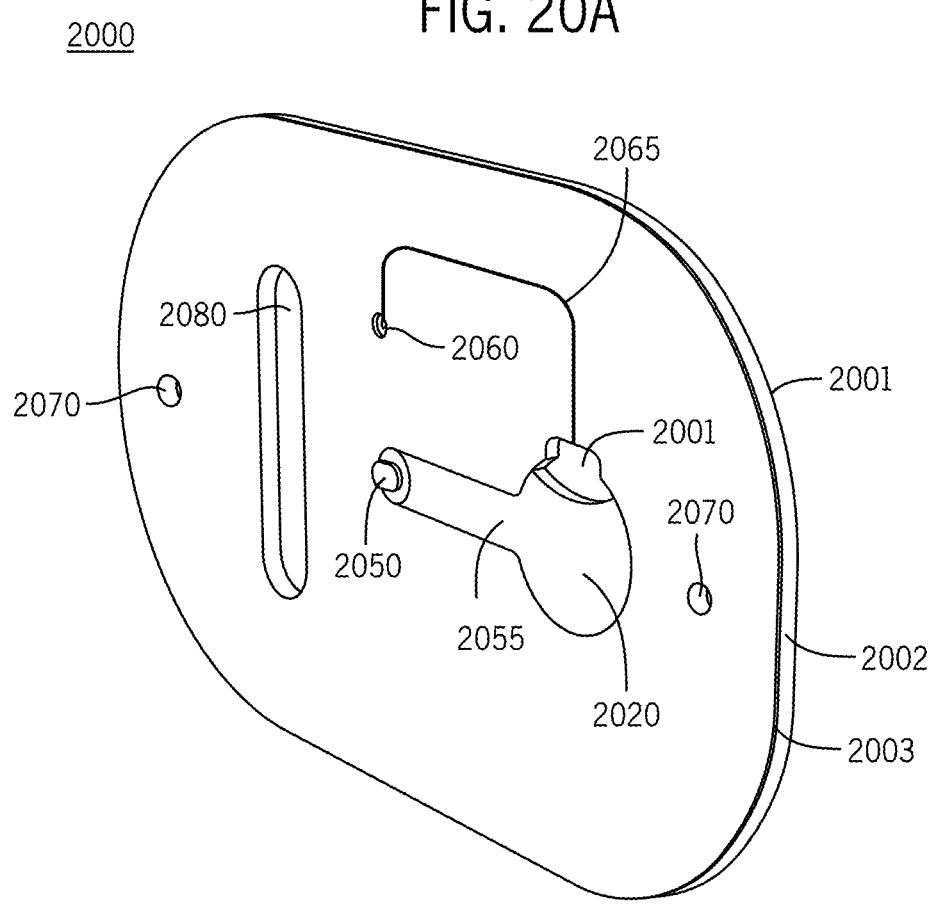
FIG. 20A-C. Drawings depicting an exemplary sample holder 2000 comprising (A) a back/bottom layer 2001, center layer 2002, front/top layer 2003, sample container 2020, fluid port 2050, fluid channel 2055, air vent 2060, vent channel 2065, assembly guides 2070, and shuttle mechanism engagement slot 2080; (B) a back/bottom layer 2001, center layer 2002, front/top layer 2003, and front/top support layer 2004; and (C) port/vent cover 2068.
Figure 20B:
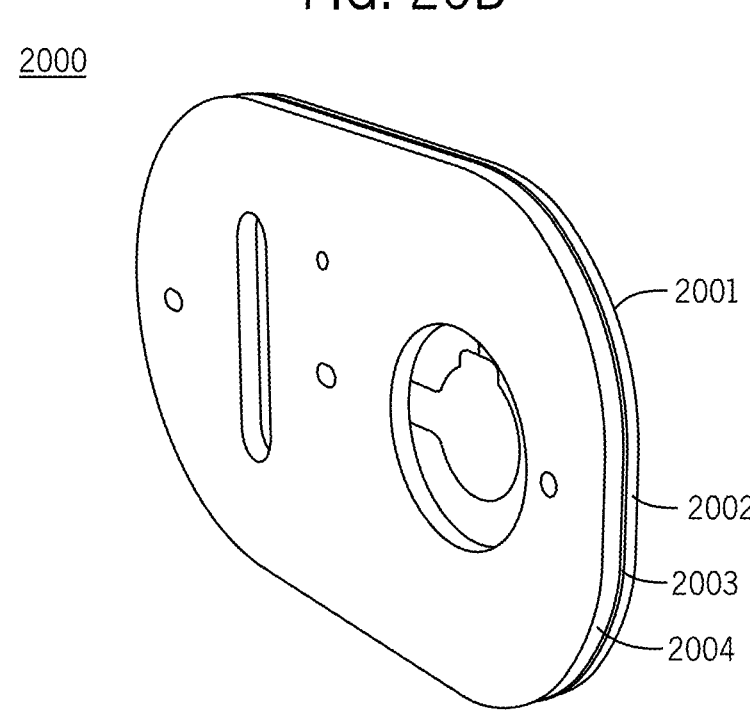
Figure 20C:
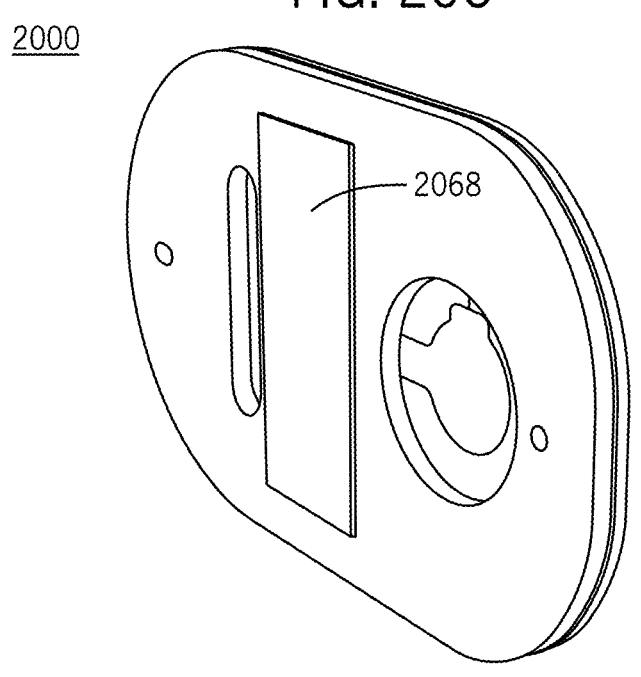

FIG. 20A-D depicts an exemplary sample holder 2000 comprising various components. The sample holder comprises a card made from multiple separate layers. Holes and other cutouts within the different layers create ports, vents channels, sample containers and other elements on/in the card. The various layers are sealed/bonded together to form a single sample holder. The exemplary sample holder of FIG. 20 (also depicted in FIG. 21) is configured to be mounted vertically onto a device, such that gravity is directed across the width (e.g., diameter) of the sample container, not vertically through the depth of the container. In some embodiments, vertical mounting of the sample holder on a device (e.g., a device comprising a shuttling mechanism) facilitates filling with liquids and removal of air. Liquid flow into the slide is improved because of the hydrostatic pressure; air flow out is improved because of differences in density between the liquid and air (FIG. 20A).

In some embodiments, devices herein provide efficiency in heating/cooling a sample, for example, by maximizing the ratio of sample volume to container materials. In some embodiments, the available space within the sample container is filled at least 50% (e.g., 50%, 60%, 70%, 80%, 90%, 95%, 99%, 100%, or ranges therebetween) with sample. In some embodiments, container materials are thin (e.g., <1 mm, <0.5 mm, <0.2 mm, <0.1 mm, <0.05 mm, <0.02 mm, <0.01 mm). In some embodiments, the ratio of sample mass to container mass is 100:1, 90:1, 80:1, 70:1, 60:1, 50:1, 40:1, 30:1, 20:1, 10:1, 9:1, 8:1, 7:1, 6:1, 5:1, 4:1, 3:1, 2:1, 1:1, or ranges therebetween.

Any suitable type of container may find use in embodiments herein. For example, a sample may be contained within a well, tube, chamber, reservoir, capsule, channel, etc. The container may be formed of a single material and/or a single piece of material (e.g., molded or manufactured to be a single piece container), or may comprise multiple materials and/or pieces (e.g., separately manufactured pieces).

In some embodiments, a sample container is a thin (e.g., 5 mm or less (e.g., 5 mm, 4 mm, 3 mm, 2 mm, 1 mm, 0.75 mm, 0.5 mm, 0.4 mm, 0.3 mm, 0.25 mm, 0.2 mm, 0.175 mm, 0.15 mm, 0.125 mm, 0.1 mm, 0.075 mm, 0.05 mm, 0.025 mm, 0.01 mm, or less, or ranges therebetween (e.g., 3 mm or less, 0.1 to 0.25 mm, etc.))) well sandwiched between two (e.g., top/front and bottom/back) surfaces. In some embodiments, the cross-sectional shape of the well is circular, square, rectangular, hexagonal, or any other suitable shape. In some embodiments, the cross-sectional dimensions of the well are greater than the thickness to facilitate close proximity of the entirety of a sample within the container to temperature regulators. In some embodiments, the cross-sectional dimensions of the well are 1-20 mm (e.g., 1 mm, 2 mm, 3 mm, 4 mm, 5 mm, 6 mm, 7 mm, 8 mm, 9 mm, 10 mm, 12 mm, 14 mm, 16 mm, 17 mm, 18 mm, 20 mm, or ranges therebetween (e.g., 5-10 mm)).

In some embodiments, a sample container attaches to, or is held by, a sample holder (the sample holder, in turn engages with the shuttling mechanism). In other embodiments, the sample container is part of a sample holder. For example, in some embodiments, a sample holder comprises multiple layers; a central layer contains a void, that when placed between top/front and bottom/back layers, produces a reservoir that serves as a sample container. The top/front and/or bottom/back layers may be rigid (e.g., plastic) materials, a membrane or film, or some combination thereof. The size of the sample container depends upon the dimensions of the void, and the thickness of the central layer. FIGS. 7 and 20 depict exemplary sample holders (e.g., cartridge style) that utilizes variants of this architecture.

In some embodiments, a sample container comprises a port or opening for adding a sample to the sample container. In some embodiments, a port or other opening comprises a hole in a exterior layer of the sample holder (e.g., front/top layer or back/bottom layer) that alignes with the opening in the center layer. In some embodiments, the sample container and/or sample holder comprises an element/mechanism for closing the port/opening (e.g., lid, cap, membrane, etc.). In some embodiments, the container is sealed, after addition of a sample to the container. As depicted in FIG. 7, in some embodiments, altering the position (e.g., sliding) of the central layer of an exemplary sample holder, with respect to the top layer and/or bottom layer, results in closure/sealing of the sample container.

In some embodiments, a sample container generates capillary forces to either draw a sample into the container and/or to maintain the position of the sample within the container. In some embodiments, capillary forces are generated by the sides/bottom of a container (e.g., well) and/or by employing porous materials (e.g., membranes having pores). In embodiments where the surfaces of the container generate capillary forces, they may be increased by coating the surface to increase its surface energy. Such coatings include anti-fog solutions such as Baltic Nanotechnologies Hendlex Antifog, Microclair Sports Anit-fog Treatment, and similar solutions. In embodiments of the devices herein that employ porous materials, capillary forces are generated by surfaces in the pores. This has the advantage of generating large capillary pressures without unduly constraining the dimensions of the container. While such architectures may be preferred in some embodiments, traditional wells/containers may also be employed. Any type of porous material able to provide the capillary forces may be employed. Such porous materials include nylon, nitrocellulose, mixed cellulose esters, polysulfones, and the like. A fibrous membrane, such as, for example, glass, polyester, cotton, or spun polyethylene may be used. In some embodiments, reagents (e.g., PCR reagents) are dried down in the porous material and are subsequently rehydrated upon addition of the sample or buffer. In some embodiments, a container comprises a hydrogel that swells upon addition of a liquid sample.

In some embodiments, a sample container comprises any materials that are suitable for containing a liquid sample, heating/cooling a sample, are non-reactive, are easily disposable, and/or are inexpensive. Suitable materials include plastics, metals, films, membranes, etc. In some embodiments, a sample container, as well as the sample holder and other components of the devices systems herein, comprise: one or more plastics including but not limited to Bakelite, neoprene, nylon, PVC, polystyrene, polyacrylonitrile, PVB, silicone, rubber, polyamide, synthetic rubber, vulcanized rubber, acrylic, polyethylene, polypropylene, polyethylene terephthalate, polytetrafluoroethylene, gore-tex, polycarbonate, etc.; non-plastic components, such as glass, textiles (e.g., from animal, plant, mineral, and/or synthetic sources), etc.; TEFLON, HDPE, nylon, PEEK, PTFE, and/or PEBAX; or other suitable materials. In some embodiments, a sample container, sample holder, and/or other components of the devices systems herein, comprise cyclo olefin polymer (COP) and/or coated polyester (KIMOTO CARBONFEATHER) or polypropylene films (e.g., ITW/FORMEX GK-10). In some embodiments, a sample container, as well as the sample holder and other components of the devices systems herein, comprise: one or more metals, including but not limited to aluminum, antimony, boron, cadmium, cesium, chromium, cobalt, copper, gold, iron, lead, lithium, manganese, mercury, molybdenum, nickel, platinum, palladium, rhodium, silver, tin, titanium, tungsten, vanadium, zinc, and alloys thereof. In some embodiments, materials for the sample container holder are selected: to provide increased thermal transfer to the sample (e.g., from a temperature zone and/or heater), to provide sufficient mechanical strength to allow shuttling of the container in/on the device, to provide low cost, to provide low weight, and/or to provide low reactivity with sample components, etc. In some embodiments, the various layers of a sample holder are bonded to each other using one or more adhesives. In some embodiments, an adhesive is a transfer adhesive tape or double-coated tape, such as 3M™ Silicone Adhesive Transfer Tape 91022, 3M™ Silicone Double Coated Tape 96042, Adhesive Research Silicone Transfer Film ARcare 7876, etc. In some embodiments, an adhesive is epoxy, silicone-based, cyanoacrylates, urethanes adhesives, acrylic adhesives, rubber cements, pressure sensitive adhesives, heat sensitive adhesives, thermosetting structural adhesives, UV-curing adhesives, acrylic, foam, latex sealants, polysulfide sealants, polyurethane sealants, etc.

In some embodiments, a sample container comprises materials that are thermally conductive (e.g., metal (e.g., aluminum, etc.), etc.). In some embodiments, the materials that are adjacent to or in contact with a temperature regulator (e.g., heater) while the sample container is in the temperature zone are thermally conductive. In some embodiments, materials surrounding the container (e.g., those not adjacent to or in contact with a temperature regulator (e.g., heater) while the sample container is in the temperature zone) are insulators (e.g., polymers, plastics, etc.). In some embodiments, materials surrounding the container are selected based on rigidity, cost, weight, reduce autofluorescence, etc.

In some embodiments, one or more of the layers that comprise the sample container (e.g., front/top layer, center layer, bottom/back layer, support layer, etc.) and/or other components of a sample holder or device herein comprise cyclo olefin polymer (COP) or cyclic olefin copolymers (COC; Shin et al. Pure Appl. Chem., Vol. 77, No. 5, pp. 801-814, 2005; herein incorporated by reference in its entirety) of a desired thickness (e.g., 10-500 μm, 10 μm, 15 μm, 20 μm, 25 μm, 30 μm, 35 μm, 40 μm, 50 μm, 60 μm, 70 μm, 80 μm, 90 μm, 100 μm, 125 μm, 150 μm, 175 μm, 200 μm, 250 μm, 300 μm, 400 μm, 500 μm, or ranges therebetween).

In some embodiments, one or more surfaces of a sample container are coated to impart one or more desired characteristics and/or functionalities. A hydrophobic coating may be used on one or more surfaces of the sample container, for example, to reduce sample loss. Suitable hydrophobic coatings include paralyene, polytetrafluoroethylene, etc.

While the various components of the systems/devices herein may be constructed from any desired material, in certain embodiments, all or a portion of the sample holder (e.g., discs, arms, etc.) and/or sample container is constructed from injection-molded pieces with heat-sealed cover films.

In some embodiments, the sample container is attached to and/or resides on/in a sample holder. In some embodiments, the sample holder is also attached to the shuttling mechanism, and thereby translates the movement of the shuttling mechanism into the proper positioning of the sample container in the various preparation/analysis zones. In some embodiments, the holder positions the sample container in a stationary positon and the various preparation/analysis zones are moved. A sample holder may be of any suitable shape, examples include a disc, arm, cartridge/cassette, etc. In some embodiments, a holder is removably attachable to a system/device. For example, the holder may be attached at the shuttling mechanism for use, and removed from the shuttling mechanism for addition of the sample to the sample container. In some embodiments, the sample holder is permanently affixed to the device, for example, via the shuttling mechanism.

In some embodiments, a sample container is removably attachable to a sample holder. In some embodiments, a sample container is within a sample holder. In some embodiments, a sample container is a component of a sample holder. In some embodiments, a sample holder comprises a single sample container and/or a single point of attachment for a sample container. In other embodiments, a sample holder comprises multiple sample containers and/or a multiple points of attachment for a sample containers (e.g., 2, 3, 4, 5, 6, 7, 8, 9, 10, 12, 16, or more or ranges therebetween). In some embodiments, multiple sample containers facilitate multiplex reactions and/or multiple reactions performed in parallel.

In some embodiments, a sample holder comprises one or more vents and ports for introducing samples and/or reagents into a sample container on/in the holder. In some embodiments, one or more reagents (e.g., PCR reagents) are dried on the interior of a sample container.

In some embodiments, a sample holder comprises a loading position and a processing position. For example, in FIGS. 7 and 11, it can be seen that when the void of the central layer is aligned with the opening in the adjacent layer, the holder is in the sample loading position; sliding or rotating the central layer to un-align the void of the central layer with the opening in the adjacent layer places the holder in the processing position.

Embodiments herein comprise a shuttling mechanism for moving the sample container between preparation/analysis zones. In some embodiments, the shuttling mechanism provides automated (e.g., electrically or battery driven) movement of the sample holder/container. The shuttling mechanism may comprise one or more of a stepper motor, an actuator, a servo, magnets, a DC motor, etc. In some embodiments, the shuttling mechanism comprises a position sensor. In some embodiments, the shuttling mechanism comprises an electrically-driven motor and/or servo that moves the sample holder to desired positions (and for desired times), thereby aligning the sample container in the desired preparation/analysis zones. Any suitable type of mover or actuator, such as servo motors, geared motors, solenoids, piezo-electric devices, magnet drives, shape memory materials, etc., may find use in the shuttling mechanisms herein. In some embodiments, the shuttling mechanism is manually-driven. For example, a hand crank may be used to power the device, generating the power to heat the temperature zones and/or drive the shuttle mechanism. In some embodiments, the shuttling mechanism facilitates movement of the sample holder/container between the temperature zones and/or detector by hand.

As described throughout, the devices/systems herein physically shuttle a sample container (and sample) between two or more preparation/analysis zones, by movement of the sample container and/or the preparation/analysis zones. In some embodiments, one or more of the preparation/analysis zones are temperature zones. In some embodiments, the sample container is placed into a position in/on the device that maintains a regulated temperature by movement of the sample container and/or the preparation/analysis zones. In some embodiments, the temperature zone maintains a defined temperature. In some embodiments, the defined temperature is between 0° C. and 100° C. (e.g., 1° C., 5° C., 10° C., 15° C., 20° C., 25° C., 30° C., 35° C., 40° C., 45° C., 50° C., 55° C., 60° C., 65° C., 70° C., 75° C., 80° C., 85° C., 90° C., 95° C., 99° C., or ranges (e.g., 50-99° C.) or temperatures (e.g., 67° C.) therebetween). In some embodiments, the temperature of a temperature zone is maintained by a temperature regulator. In some embodiments, the temperature regulator comprises a heating element (heater) and/or a cooling element. Although most embodiments herein are described as comprising heaters as temperature regulators, other temperature regulators (e.g., coolers, fans, etc.) may find use in any suitable embodiments herein. In some embodiments, a fluid (e.g., coolant) of a particular temperature is used as a temperature regulator. In some embodiments, a fan is employed as a temperature regulator. The heaters or heating elements described in specific embodiments herein may be replaced by alternative thermal regulators (e.g., coolers, fans, fluid temperature regulators, solid-state temperature regulators, etc.) within the scope of embodiments herein.

In some embodiments, a temperature zone comprises a single heater. In some embodiments, a temperature zone comprises two heaters. In some embodiments, the sample container is placed adjacent to and/or in direct contact with a heater or heaters within a temperature zone. In some embodiments, the close proximity (e.g., direct contact) to the heater(s) rapidly (e.g., 20 seconds, 18 seconds, 16 seconds, 14 seconds, 12 seconds, 10 seconds, 9 seconds, 8 seconds, 7 seconds, 6 seconds, 5 seconds, 4 seconds, 3 seconds, 2 seconds, 1 second, or ranges therein (e.g., 2-6 seconds)) brings the sample container (and sample) to the temperature of the heater(s). In some embodiments, the shuttling mechanism moves the sample container (e.g., via the sample holder) into the temperature zone. In some embodiments, the shuttling mechanism moves the temperature zone into the proximity of (e.g., contact with) the sample container. In some embodiments, one or more heaters are movable within the device. In some embodiments, once the sample container is brought into the temperature zone, the heater is moved to directly contact and/or envelop the sample container.

In some embodiments, a temperature zone comprises two heaters. In some embodiments, each heater comprises a sample contacting face (or sample presenting face); this is the portion of the heater that is adjacent to, or in contact with, the sample container when the sample container is properly aligned within the temperature zone. In some embodiments, two heaters are aligned within a temperature zone such that their sample presenting faces are opposed to each other, creating a gap between the sample presenting faces within which the sample container is configured (e.g., sized, oriented on the device, etc.). In some embodiments, when the sample container is shuttled into the temperature zone (e.g., by movement of the sample container and/or of the temperature zone), two sides of the container (e.g., top and bottom) are each adjacent to sample presenting faces of the heaters. In some embodiments, upon shuttling of the sample container into the temperature zone, one or both heaters are physically moved toward each other, narrowing the gap within which the container resides. In some embodiments, movement of the heater(s) results in contact between the heater(s) and the sample container.

As described throughout, the devices/systems herein physically shuttle a sample container (and sample) between two or more preparation/analysis zones (e.g., by movement of the sample container and/or of the temperature zone). In some embodiments, a preparation/analysis zone is a detection zone. In some embodiments, the sample container is shuttled into the detection zone, and one or more characteristics of the sample are quantified/qualified. In some embodiments, the detection zone is shuttled into alignment with the sample container, and one or more characteristics of the sample are quantified/qualified. In particular embodiments, the color, fluorescence, luminescence of the sample is detected. In some embodiments, a detection zone comprises a luminometer, a fluorimeter, a spectrophotometer, chromatograph, microscope, fluorescence imager, digital imager, etc.

In embodiments, systems and/or devices herein, including their components, operate under computer or other electronic control. For example, a processor is included with or in the system and/or its components and functions described herein using software, firmware, hardware (e.g., fixed logic circuitry), manual processing, or a combination thereof. The terms "controller" "functionality," "service," and "logic" as used herein generally represent software, firmware, hardware, or a combination of software, firmware, or hardware in conjunction with controlling the systems, devices, and/or components herein. In the case of a software implementation, the module, functionality, or logic represents program code that performs specified tasks when executed on a processor (e.g., CPU or CPUs). The program code may be stored in one or more computer-readable memory devices (e.g., memory and/or one or more tangible media), and so on. The structures, functions, approaches, and techniques described in this document can be implemented on a variety of commercial computing platforms having a variety of processors. Processors are not limited by the materials from which they are formed or the processing mechanisms employed therein. For example, the processor may be comprised of semiconductor(s) and/or transistors (e.g., electronic integrated circuits (ICs)). Memory can be included with the processor. The memory can store data, such as a program of instructions for operating multiple systems, the system and/or system components, data, and so on. Although a single memory device can be used, a wide variety of types and combinations of memory (e.g., tangible memory, non-transitory memory) may be employed, such as random access memory (RAM), hard disk memory, removable medium memory, external memory, and other types of computer-readable storage media.

In some embodiments, a processor, CPU, or other electronic-based controller(s) directs the shuttling mechanism to move the sample container through the two or more preparation/analysis zones, and directs the performance of those zones (e.g., maintenance of a desired temperature, obtaining an image of the sample, etc.). For example, the controller provides instructions to maintain the heater(s) of a first temperature zone at 95° C. and a second temperature zone at 60° C. The controller directs the shuttling mechanism to oscillate the sample container between the two temperature zones for defined time periods and for a defined number of times. Given the proper sample and reagents in the sample container (e.g., target nucleic acid, nucleotides, primers, buffer, magnesium, polymerase, etc.), movement of the sample through two temperature zones results in amplification of the target nucleic acid. In some embodiments, a user provides instructions to a processor in order to set the characteristics of the preparation/analysis zones and the desired movement (e.g., order, time periods, cycles, etc.) of the sample container through the zones.

In some embodiments, a processor, CPU, or other electronic-based controller(s) directs the shuttling mechanism to move the the two or more preparation/analysis zones into alternating proximity with the sample container, and directs the performance of those zones (e.g., maintenance of a desired temperature, obtaining an image of the sample, etc.). For example, the controller provides instructions to maintain the heater(s) of a first temperature zone at 95° C. and a second temperature zone at 60° C. The controller directs the shuttling mechanism to oscillate the two temperature zones in proximity with the sample container for defined time periods and for a defined number of times. Given the proper sample and reagents in the sample container (e.g., target nucleic acid, nucleotides, primers, buffer, magnesium, polymerase, etc.), movement of the sample through two temperature zones (by movement of the temperature zones) results in amplification of the target nucleic acid. In some embodiments, a user provides instructions to a processor in order to set the characteristics and movement of the preparation/analysis zones.

The systems/devices herein find use in a variety of sample preparation/analysis methods and applications. A sample is rapidly exposed to multiple conditions and/or analysis techniques, without removing the sample from the sample container. Many embodiments described herein relate to exposing a sample to multiple temperatures (e.g., thermal cycling). Although the systems/devices described herein are not necessarily limited to such embodiments, uses for such embodiments are further described.

In some embodiments, a sample for use with the devices and methods herein comprises one or more nucleic acids (e.g., DNA, RNA, etc.). In some embodiments, the sample contains or is suspected to contain a target nucleic acid sequence. In some embodiments, methods are provided for the amplification, detection, quantification, etc. of one or more nucleic acids (e.g., target nucleic acids) within a sample. In some embodiments, various polymerase chain reaction (PCR) methods are employed using the devices and methods herein.

The devices and methods herein are useful for performing PCR. Certain basic principles of PCR that may find use in embodiments herein are described, for example, in U.S. Pat. Nos. 4,683,195; 4,683,202; 4,800,159; and 4,965,188; incorporated by reference in their entireties. Basic PCR is used to amplify a sample of target DNA for analysis or other uses. PCR uses multiple cycles of denaturation, annealing of primer pairs to opposite strands, and primer extension to exponentially increase copy numbers of a target nucleic acid sequence. The basic PCR reaction involves copying the strands of the target DNA and then using the copies to generate additional copies in subsequent cycles. The temperature of a double-stranded target DNA is elevated to denature the DNA (e.g., 85° C., 86° C., 87° C., 88° C., 89° C., 90° C., 91° C., 92° C., 93° C., 94° C., 95° C., 97° C., 98° C., 99° C., or ranges therebetween (e.g., 92-97° C.)) and the temperature is then reduced to anneal at least one primer to each strand of the denatured target DNA (e.g., 48° C., 50° C., 52° C., 54° C., 56° C., 58° C., 60° C., 61° C., 62° C., 63° C., 64° C., 65° C., 66° C., 67° C., 68° C., 69° C., 70° C., 72° C., 74° C., or ranges therebetween (e.g., 62-72° C.)). In some embodiments, primers are used as a pair—a forward primer and a reverse primer—and can be referred to as a primer pair or primer set. In some embodiments, the primer set comprises a 5' upstream primer that can bind with the 5' end of one strand of the denatured target DNA and a 3' downstream primer that can bind with the 3' end of the other strand of the denatured target DNA. Once a given primer binds to the strand of the denatured target DNA, the primer is extended by the action of a polymerase (e.g., at the annealing temperature or at a distinct extension temperature (e.g., 65° C., 66° C., 67° C., 68° C., 69° C., 70° C., 71° C., 72° C., 73° C., 74° C., 75° C., or ranges therebetween). In some embodiments, the polymerase is a thermostable DNA polymerase, for example, a Taq polymerase (or suitable variants thereof (e.g., AMPLITAQ GOLD, CRIMSON TAQ, DEEP VENT$_R$, etc.)). The product of extension, which sometimes may be referred to as an amplicon, is then denatured from the resultant strands and the process can be repeated. In some embodiments, the devices and methods provided herein are useful for the cycling of a nucleic-acid-containing sample through the various temperature steps of a PCR reaction.

In some embodiments, a device comprises two temperature zones, and the sample container is shuttled between the zones for prescribed time periods (e.g., by movement of the sample container or the temperature zones). In some embodiments, a first temperature zone is of a temperature suitable for denaturing a target nucleic acid and any primers or probes present in the sample. In some embodiments, a sample container is maintained in the first temperature zone for 1-30 seconds (e.g., 1, 2, 3, 4, 5, 6, 7, 8, 9, 10, 12, 14, 16, 18, 20, 25, 30, or any times or ranges therebetween (e.g., 2-8 seconds)). In some embodiments, a second temperature zone is of a temperature suitable for annealing primer(s) to a target nucleic acid and allowing a polymerase to synthesize a new complimentary strand (e.g., extension). In some embodiments, a sample container is maintained in the second temperature zone for 1-30 seconds (e.g., 1, 2, 3, 4, 5, 6, 7, 8, 9, 10, 12, 14, 16, 18, 20, 25, 30, or any times or ranges therebetween (e.g., 2-8 seconds)). In some embodiments, the sample container is shuttled between the two temperature zones for 2-50 cycles (e.g., 2, 4, 6, 8, 10, 12, 15, 20, 25, 30, 35, 40, 45, 50, or values or ranges therebetween). In some embodiments, the time to shuttle the sample container between zones is 1 second or less (e.g., 1 second, 0.75 seconds, 0.5 seconds, 0.4 second, 0.3 seconds, 0.2 seconds, 0.1 seconds, or less, or ranges therebetween (e.g., 0.5 seconds or less)).

In some embodiments, a device comprises three temperature zones, and the sample container is shuttled between the zones for prescribed time periods. In some embodiments, the three temperature zones are alternatively brough into proximity of the sample container for prescribed time periods. In some embodiments, a first temperature zone is of a temperature suitable for denaturing a target nucleic acid and any primers or probes present in the sample. In some embodiments, a sample container is maintained in the first temperature zone for 1-30 seconds (e.g., 1, 2, 3, 4, 5, 6, 7, 8, 9, 10, 12, 14, 16, 18, 20, 25, 30, or any times or ranges therebetween (e.g., 2-8 seconds)). In some embodiments, a second temperature zone is of a temperature suitable for annealing primer(s) to a target nucleic acid. In some embodiments, a sample container is maintained in the second temperature zone for 1-30 seconds (e.g., 1, 2, 3, 4, 5, 6, 7, 8, 9, 10, 12, 14, 16, 18, 20, 25, 30, or any times or ranges therebetween (e.g., 2-8 seconds)). In some embodiments, a third temperature zone is of a temperature suitable for allowing a polymerase to synthesize a new complimentary strand (e.g., extension). In some embodiments, a sample container is maintained in the second temperature zone for 1-30 seconds (e.g., 1, 2, 3, 4, 5, 6, 7, 8, 9, 10, 12, 14, 16, 18, 20, 25, 30, or any times or ranges therebetween (e.g., 2-8 seconds)). In some embodiments, the sample container is shuttled between the three temperature zones for 2-50 cycles (e.g., 2, 4, 6, 8, 10, 12, 15, 20, 25, 30, 35, 40, 45, 50, or values or ranges therebetween). In some embodiments, the time to shuttle the sample container between zones is 1 second or less (e.g., 1 second, 0.75 seconds, 0.5 seconds, 0.4 second, 0.3 seconds, 0.2 seconds, 0.1 seconds, or less, or ranges therebetween (e.g., 0.5 seconds or less)).

In some embodiments, devices and methods herein are capable of performing a 40 cycle amplification reaction (e.g., 2 temperature zones and 1 detector) in 15 minutes or less (e.g., 15 minutes, 14 minutes, 15 minutes, 15 minutes, 15 minutes, 15 minutes, 15 minutes, 15 minutes, 15 minutes, 15 minutes, 15 minutes, or less, or ranges therein (e.g., 6-10 minutes, 12 minutes or less, etc.).

In some embodiments, the devices and methods find use in performing variations on PCR or other amplification techniques that utilize cycling through multiple temperatures. For example, in a variation called reverse transcriptase PCR (RT-PCR), reverse transcriptase (RT) is used to make a complementary DNA (cDNA) from mRNA, and the cDNA is then amplified by PCR to produce multiple copies of DNA. In some embodiments, PCR is digital PCR, sec, e.g., Vogelstein, B., & Kinzler, K. W. (1999) "Digital PCR" Proc. Natl. Acad. Sci. USA 96:9236-9241; herein incorporated by reference in its entirety. The ligase chain reaction (Weiss, R., Science 254: 1292 (1991), herein incorporated by reference in its entirety), commonly referred to as LCR, uses two sets of complementary DNA oligonucleotides that hybridize to adjacent regions of the target nucleic acid. The DNA oligonucleotides are covalently linked by a DNA ligase in repeated cycles of thermal denaturation, hybridization and ligation to produce a detectable double-stranded ligated oligonucleotide product. Strand displacement amplification (Walker, G. et al., Proc. Natl. Acad. Sci. USA 89: 392-396 (1992); U.S. Pat. Nos. 5,270,184 and 5,455,166, each of which is herein incorporated by reference in its entirety), commonly referred to as SDA, uses cycles of annealing pairs of primer sequences to opposite strands of a target sequence, primer extension in the presence of a dNTPaS to produce a duplex hemiphosphorothioated primer extension product, endonuclease-mediated nicking of a hemimodified restriction endonuclease recognition site, and polymerase-mediated primer extension from the 3' end of the nick to displace an existing strand and produce a strand for the next round of primer annealing, nicking and strand displacement, resulting in geometric amplification of product. Thermophilic SDA (tSDA) uses thermophilic endonucleases and polymerases at higher temperatures in essentially the same method (EP Pat. No. 0684315; incorporated by reference in its entirety). Any suitable amplification techniques that utilize temperature changes and/or thermal cycling may be performed using the devices and methods described herein. For further discussion of known amplification methods, sec Persing, David H., "In Vitro Nucleic Acid Amplification Techniques" in Diagnostic Medical Microbiology: Principles and Applications (Persing et al., Eds.), pp. 51-87 (American Society for Microbiology, Washington, D C (1993); incorporated by reference in its entirety).

Recently, the ability to measure the kinetics of a PCR reaction by real-time detection has allowed for accurate and precise quantification of nucleic acid sequences with high sensitivity in a process known at quantitative PCR (qPCR) or real-time PCR (RT-PCR). This has become possible by detecting the PCR products through fluorescence monitoring and measurement of PCR product during the amplification process, for example, by fluorescent dual-labeled hybridization probe technologies, such as the TAGMAN 5' fluorogenic nuclease assay described by Holland et al. (Proc. Natl. Acad. Sci. U.S.A. 88, 7276 (1991)), Gibson et al. (Genome Res. 6, 99 (1996)), and Heid et al. (Genome Res. 6, 986 (1996)); or "Molecular Beacons" (Tyagi, S. and Kramer, F. R. Nature Biotechnology 14, 303 (1996)); incorporated by reference in their entireties. Nazarenko et al. (Nucleic. Acids Res. 25, 2516 (1997); incorporated by reference in its entirety) have described use of dual-labeled hairpin primers, as well as recent modifications utilizing primers labeled with only a single fluorophore (Nazerenko et al., Nucleic. Acids Res. (2002); incorporated by reference in its entirety). One of the more widely used methods is the addition of double-strand DNA-specific fluorescent dyes to the reaction such as: ethidium bromide (Higuchi et al., Biotechnology (1992) and Higuchi et al., Biotechnology 11, 102610, 413 (1993)), YO-PRO-1 (Ishiguro et at., Anal. Biochem. 229, 207 (1995)), or SYBR Green I (Wittwer et al., Biotechniques 22,130 (1997)); incorporated by reference in their entireties. These improvements in the PCR method have provided for simultaneous amplification and homogeneous detection of amplified nucleic acids without purification of PCR product or separation by gel electrophoresis. This combined approach decreases sample handling, saves time, and greatly reduces the risk of product contamination for subsequent reactions, as there is no need to remove the samples from their closed containers for further analysis.

The general principles for template quantification by real-time PCR were disclosed by Higuchi et al., Bio/Technology 10:413-417, 1992; Higuchi et al., Bio/Technology 11:1026-1030; incorporated by reference in their entireties. This approach for quantitative PCR utilizes a double-strand specific fluorescent dye, ethidium bromide, added to amplification reaction. The fluorescent signal generated at each cycle of PCR is proportional to the amount of PCR product. A plot of fluorescence versus cycle number is used to describe the kinetics of amplification and a fluorescence threshold level was used to define a fractional cycle number related to initial template concentration. Specifically, the log of the initial template concentration is inversely proportional to the fractional cycle number (threshold cycle, or Ct), defined as the intersection of the fluorescence versus cycle number curve with the fluorescence threshold. Higher amounts of starting template results in PCR detection at a lower Ct value, whereas lower amounts require a greater number of PCR cycles to achieve an equivalent fluorescent threshold (Ct) and are detected at higher Ct values. Typically, the setting of this fluorescence threshold is defined as a level that represents a statistically significant increase over background fluorescent noise. Since this occurs at an early stage in the PCR process when critical substrates are not limiting, quantification of starting template occurs over a broad dynamic range with high accuracy, precision, and sensitivity.

qPCR can be performed utilizing DNA or RNA as a starting material. For a DNA target, standard PCR protocols may be used. Quantitative reverse transcription PCR (RT-qPCR) is used when the starting material is RNA. RNA is first transcribed into complementary DNA (cDNA) by reverse transcription (e.g., from total RNA or messenger RNA (mRNA)). The cDNA is then used as the template for a qPCR reaction. In some embodiments, the devices described find use in performing one-step RT-qPCR (e.g., RT-qPCR without purifying the cDNA after reverse transcription), and can be programed to perform cycles useful for as much.

In some embodiments, qPCR utilizes a fluorescent dye that binds non-specifically to all double-stranded DNA (or all double stranded nucleic acids). For example, SYBR Green is a commonly used fluorescent DNA binding dye that binds all double-stranded DNA, and detection of which can be monitored by measuring the increase in fluorescence throughout the cycle. Increase in the intensity of SYBR Green correlates to an increase in the concentration of double stranded DNA (e.g., amplified DNA). SYBR Green I has an excitation and emission maxima of 494 nm and 521 nm, respectively. In some embodiments, a qPCR protocol comprises probe-based qPCR. Probe based QPCR relies on the sequence-specific detection of a desired PCR product. Unlike SYBR based QPCR methods that detect all double-stranded DNA, probe based QPCR utilizes a fluorescent-labeled target-specific probe resulting in increased specificity and sensitivity. Using multiple, detectably-different labelled probes allows for the detection of multiple target sequences in a single sample. In some embodiments, the devices herein find use in performing qPCR with any of the above detection methods, with any suitable dyes or probes, and with any other qPCR methods understood by the field (e.g., TAQMAN probes).

In some embodiments, the devices and methods provided herein are useful for the cycling of a nucleic-acid-containing sample through the various temperature steps of a qPCR reaction, as well as detection zone, in order to quantify a target nucleic acid and/or monitor the amplification thereof. In some embodiments, a device comprises two or three temperature zones and at least one detection zone. As described herein, the detection zone may comprise a fluorimeter, an image sensor, digital camera, CCD, or any other device capable of detecting fluorescence or creating an image of the sample container that encompasses emission wavelength of a desired fluorophore. In some embodiments, the sample container is shuttled through the temperature zones (e.g., moving the sample container or the temperature zones), as described above and elsewhere herein, and at a desired point during the cycle is moved into the detection zone, the fluorescence is measured and/or an image of the sample container is obtained, and the sample container continues through the cycle. In some embodiments, detection occurs after extension and before a denaturation. In other embodiments, detection occurs at any other regularly occurring point in a cycle. In some embodiments, a program comprises a single detection step per cycle. In some embodiments, a detection step is 5 seconds or less (e.g., 5 seconds, 4 seconds, 3 seconds, 2 second, 1 second, 0.75 seconds, 0.5 seconds, or less, or ranges therebetween (e.g., <1 second)).

In some embodiments, various reagents are provided for use in PCR, pPCR, and/or other methods using the devices described herein. Such reagents include water, buffer, dNTPs, primers, controls, catalysts (e.g., a magnesium catalyst (such as $MgCl_2$)), initiators, promoters, cofactors, enzymes (e.g., DNA polymerase, reverse transcriptase, etc.), salts, buffering agents, chelating agents, probes, fluorescent dyes, and combinations thereof.

In some embodiments, multiple qPCR reactions (e.g., detectably different dyes for multiple targets) and/or other amplification reactions are performed in a single sample container. In some embodiments, multiple qPCR reactions (e.g., detectably different dyes for multiple targets, same dyes in multiple different sample containers) and/or other amplification reactions are performed in parallel using the devices and methods described herein.

In some embodiments, the devices described herein are not limited to nucleic acid amplification, but may find use in any technique in which repeated temperature changes and/or thermal cycling find use.

There are numerous advantages to the devices and methods described herein (e.g., relative to more traditional PCR systems), such as, faster heat transfer, lower power consumption, self-filling container(s), large field of view for fluorescence readings, nucleic acid testing protocols using standard PCR reagents, dry reagents stored in same container used for reactions, large sheets of the PMC material can be coated and dried then cut out and assembled, etc.

The devices and methods described herein find use in a variety of applications, for example, diagnostic applications (e.g., point-of-care infectious disease testing), high throughput nucleic acid testing systems, environmental testing, food testing, veterinary testing, etc. Because of the low sample, time, and energy requirement do the devices and methods herein, they are useful in applications where traditional systems and protocols are not practical.

EXPERIMENTAL

Example 1

Exemplary Device

The following example describes an exemplary device and protocol for the amplification and detection of nucleic acid in a sample. While not limiting the overall scope of embodiments herein, this example provide features, elements, and steps that may find use as described in the example, or in alternative combinations and configurations within the scope herein.

A porous container shuttle (PCS) performs qPCR by shuttling a porous container (PC), filled a solution comprising target nucleic acid and reactants, between three stations: (1) high-temperature heater (e.g., 95° C.), (2) a low-temperature heater (e.g., 60° C.), and (3) a front-surface fluorimeter. The PMC is a thin disc of porous material (e.g., a glass fiber depth filter) which draws in the PCR solution via capillary action to the point of saturation of the PMC. The liquid-saturated PMC rapidly changes temperature when brought into contact with either of the heaters. Only a few seconds (e.g., 1-10 seconds) are needed for the PC's temperature to plateau at the heater's temperature. Since the heaters are of constant temperature, these few seconds represent the total time required for heat transfer.

The PMC (FIG. 6A) is held in 'blade' (FIG. 6B) cut from a thin plastic sheet (e.g., polycarbonate plastic). The blade is sandwiched between two transparent films with hydrophobic coatings on the surfaces contacting the blade and PC (FIG. 7A-C). The combination of the high capillarity of the PMC, and hydrophobic surfaces contacting it, minimizes the loss of liquid as the PMC shuttles between processing stations. In some embodiments, the PC, blade, and cover films are formed into a disposable cassette. The liquid sample is added through a hole in the top film. The blade can be coupled to a drive motor either by mechanical or magnetic means.

In some embodiments, the PMC is coated with PCR reagents and dried. They are rehydrated when the nucleic acid test solution is added to the PC. In other embodiments, reagents are added to the nucleic acid test solution and then transferred to the PMC, or transferred to the PMC separately.

In an exemplary PCR protocol, DNA or RNA is first extracted from a sample or specimen and concentrated into aqueous solution. For example, nucleic acid may be extracted from blood, loaded onto silica-coated paramagnetic particles (PMPs), and eluted into an aqueous solution. An aliquot of the nucleic acid solution is transferred through the port in the top film into the PMC (e.g., with a pipette or other liquid transfer device). Dried reagents in the PMC rehydrate and dissolve into the aqueous solution, which wicks throughout the PMC and is contained by capillary forces.

The cassette is then placed in the instrument, where the blade engages a shuttle drive motor (FIG. 8A-C). An embedded microcontroller cycles the shuttle between the three processing stations. If the target is RNA, the first processing station has its temperature set to optimize a reverse transcriptase, which makes DNA copies of the RNA targets. An exemplary sequence for each cycle is: 1) heat at 95° C. for 5 sec, 2) heat at 60° C. for 5 sec, read fluorescence.

In some embodiments, fluorescence readings are made between each cycle. In other embodiments, the sample is cycled between the two heat zones only, and the amplification is analyzed at an endpoint reading (e.g., on the device or on a separate instrument).

Example 2

Temperature Response

Figure 9A:
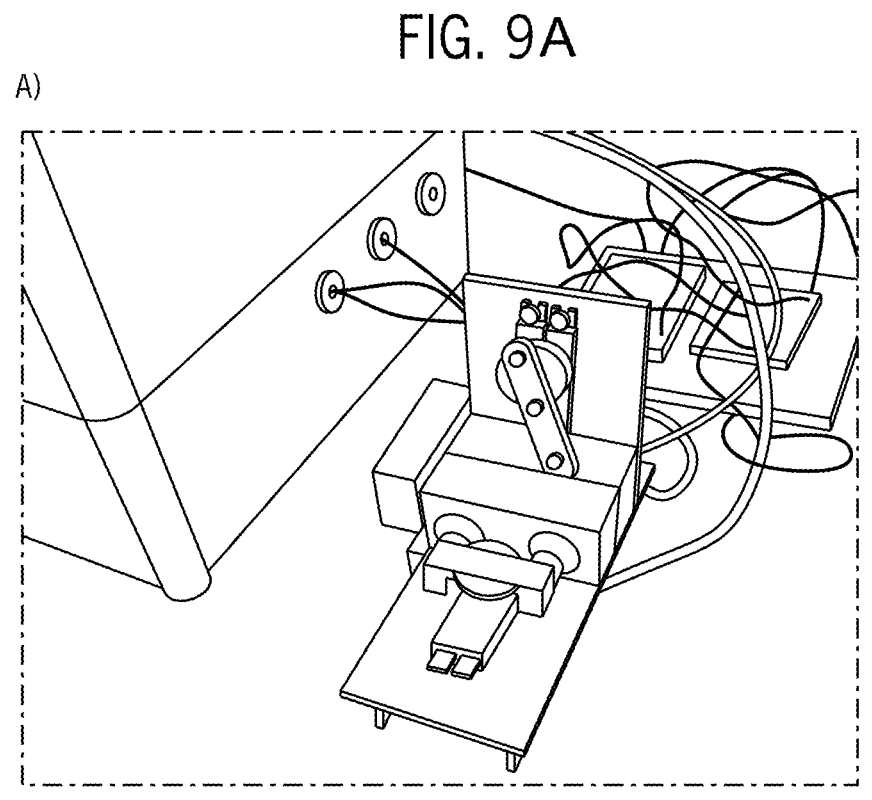
Figure 9B:
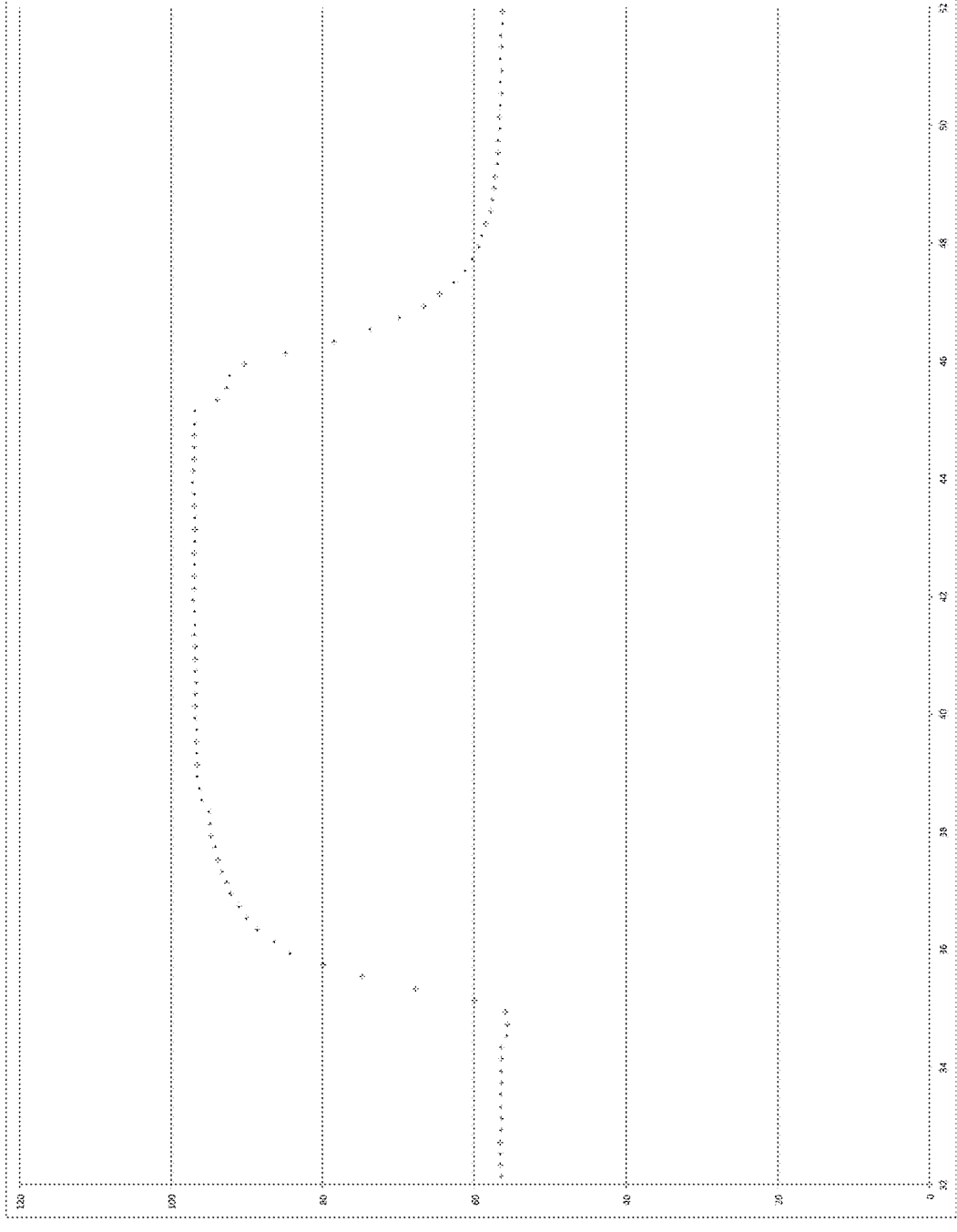
Figure 10:
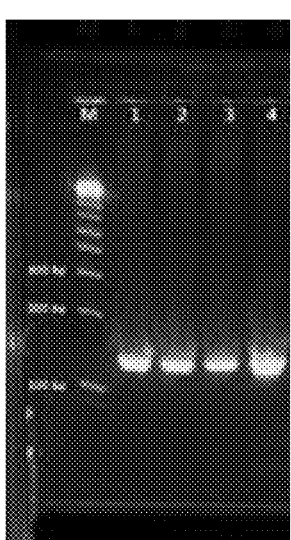
FIG. 10. Image of an agarose gel depicting a PCR reaction: performed in the exemplary device depicted in FIG. 9 (Lane 2), performed in a sample cassette of the exemplary device depicted in FIG. 9, but heated by shuttling the cassette between water baths held at 60° C. and 95° C. (Lane 3), and performed in a glass tube shuttled between the water baths held at 60° C. and 95° C. (Lane 4).
Figure 13:
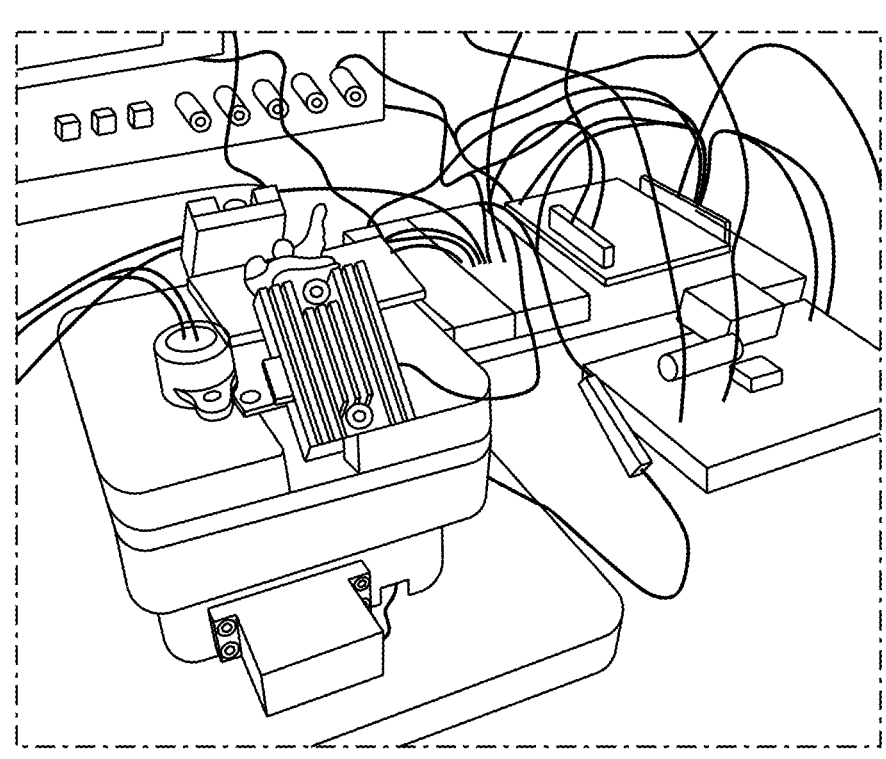
FIG. 13. Image of an exemplary system depicting the device depicted in FIG. 12, detector power supply (back left), microcontroller (center rear), LED driver (front right), and laptop computer (back right).

Using a device depicted in FIG. 9A, which is of the type depicted in FIG. 8, temperature response was measured with thermocouple inserted between two 0.25 mm thick filters (FIG. 9B). Temperature was maintained within 0.1° C. of the set points. Time to heat from 57° C. to 97° C. was 3.6 seconds, time to cool from 97° C. to 57° C. was 4.1 seconds, and the time constant was approximately 1 second.

Example 3

DNA Amplification

Experiments were conducted during development of embodiments herein (See FIG. 7) to compare DNA amplification using a device depicted in FIG. 9, which is of the type depicted in FIG. 8 (Lanes 1 and 2), versus shuttling the cassette between water baths held at 60° C. and 95° C. (Lane 3), and a positive control in a glass capillary cycled in water baths (Lane 4). Each cycle consists of 5 sec. at 95° C. and 5 sec. at 60° C. performed 40 times. The PCR reaction was collected out of the filter by a short centrifugation step, and the DNA was analyzed on a 4% agarose gel. This experiment demonstrates that the exemplary cartridges and devices are compatible with PCR and that the test bed provides amplification with the filter-based cartridge.

Example 4

Exemplary Device

The following example describes an exemplary device and protocol for the amplification and detection of nucleic acid in a sample. While not limiting the overall scope of embodiments herein, this example provide features, elements, and steps that may find use as described in the example, or in alternative combinations and configurations within the scope herein.

An exemplary PMC shuttle device is depicted in FIGS. 11-15. In this configuration, the top and bottom films are stationary, only the PMC and blade move. Advantages include: (1) elimination of a means to move the PMC away from the filling port before initiation of PCR, (2) less thermal mass to heat and cool each cycle, and (3) ability to use different materials in heat transfer areas of film from materials in fluorescence reading areas.

Example 5

Additional Device Embodiments

The following example provides additional embodiments that may find use in combination with the devices/systems described herein.

In some embodiments, holder magnets are coupled with a pair of mover magnets, for example, to reduces backlash/hysteresis. For example, two mover magnets are used to couple to opposite sides of a holder magnet. When a holder magnet is pulled across a mover magnet, it will stop at the location of the highest gradient coupling. The holder magnet is pulled back to this position when displaced further away from the mover magnet. If mover magnets are places at maximum-gradient positions on opposite sides of the holder magnet, then the three magnets provide a stable equilibrium point. When sliding friction pulls the holder magnet away from the desired position, it should return when sliding stops.

In some embodiments, component and assembly costs and weight are reduced through the use of less-rigid materials in, for example, the holder. For example, a polycarbonate plastic frame provides a sufficiently rigid cassette for use in certain embodiments herein.

In some embodiments, a sample holder is moved linearly along the cassette or device, rather than radially (FIG. 16). This linear motion reduces the footprint of the cartridge and reduces the number of mover magnets.

In some embodiments, a sample container comprises a porous media container, in which the liquid sample is absorbed by a woven material, filter pad, etc. However, in other embodiments, the solution is held in place by surface tension between the fluid and the chamber itself. For example, if the container well has diameter, D=2R, where R is the radius, and height H, and the gravitational body force is very much less than surface tension force, then the fluid will be held in the well by surface tension. Gravitational force is given by $\mu gh$, where $\rho$=density of the liquid ($\rho$=1000 kg/m$^2$), g=the gravitational constant (g=9.8 m/s2), and H=the height of the well. Surface tension force is given by $\sigma/R$, where $\sigma$ is the surface tension. The relationship between the forces can thus be written as $\rho gH \ll \sigma/R$. Solving for R gives $R \ll \sigma/\rho gH$. If H=0.5 mm, which is the 0.020" thick polycarbonate sheets we use for the blades, then $R \ll 14.7$ mm. If R is $\frac{1}{10}^{th}$, then $D \cong 3$ mm. A well of this size has a volume of 3.5 ul. 5 mm diameter wells have a volume of 20 ul. The Bond number, which is ratio of gravitational forces to surface tension force, is 0.17. If the diameter is 2 mm, the Bond number is 0.07.

In some embodiments, well depth is reduced to accommodate larger diameter wells, or is increased if the diameter gets smaller. Small diameter, deep wells are preferred from a packing standpoint, but depth increases the thermal transport path length and slows heat transfer.

In some embodiments, a plate surrounding the sample container comprises a conductive material (e.g., aluminum or another conductive metal). For example, a plate immediately surrounding the sample chambers, but not the entire sample holder, comprises a conductive metal (FIG. 17A), which allows for it to be made of good heat conductor so the sample is heated from the sides as well as the top and bottom. The temperature of the fluid in the well, midway between the top and bottom surfaces, has an exponential series time response. The coefficients of the exponential terms has thermal diffusivity in the numerator and the square of the fluid depth in the denominator. For a 0.5 mm thick pad, this model predicts it would take 3 sec to get within 5% of the heater set point with the thermal diffusivity of our materials; close to what was observed experimentally. Halving the thickness to 0.25 mm, would reduce the time to 0.75 sec.

In some embodiments, a sample holder comprises multiple sample containers (FIG. 17B). Advantage of such an arrangement include multiplexing, without being limited by dye colors, and splitting of targets to reduce the limit of detection. Performing multiple assays in a single well presents a number of challenges for both the assay and instrumentation design. Splitting the sample between multiple wells makes the reaction kinetics much simpler and more robust.

In some embodiments, fluorescence is read with a camera chip. For a silicon photodiode detector to read multiple PCR reactions in a single well, interference filters are used to separate the different dyes by wavelength and multiple LEDs are used for excitation. If each assay is performed in a separate well, then these challenges are eliminated. The trade-off is that the NAs in the sample must be split, which reduces the number of targets in each well. In some embodiments, all wells are imaged simultaneously, which reduces the reading time. In some embodiments, the images would be acquired with low-light, back-side illuminated camera chips that are commercially available.

In some embodiments, sample is transferred using a capillary device, which eliminates the need for a pipette to use the device. Capillary forces are used to transfer the sample from a pretreatment well to a PCR well.

Example 6

Paramagnetic Particles

Figure 22:
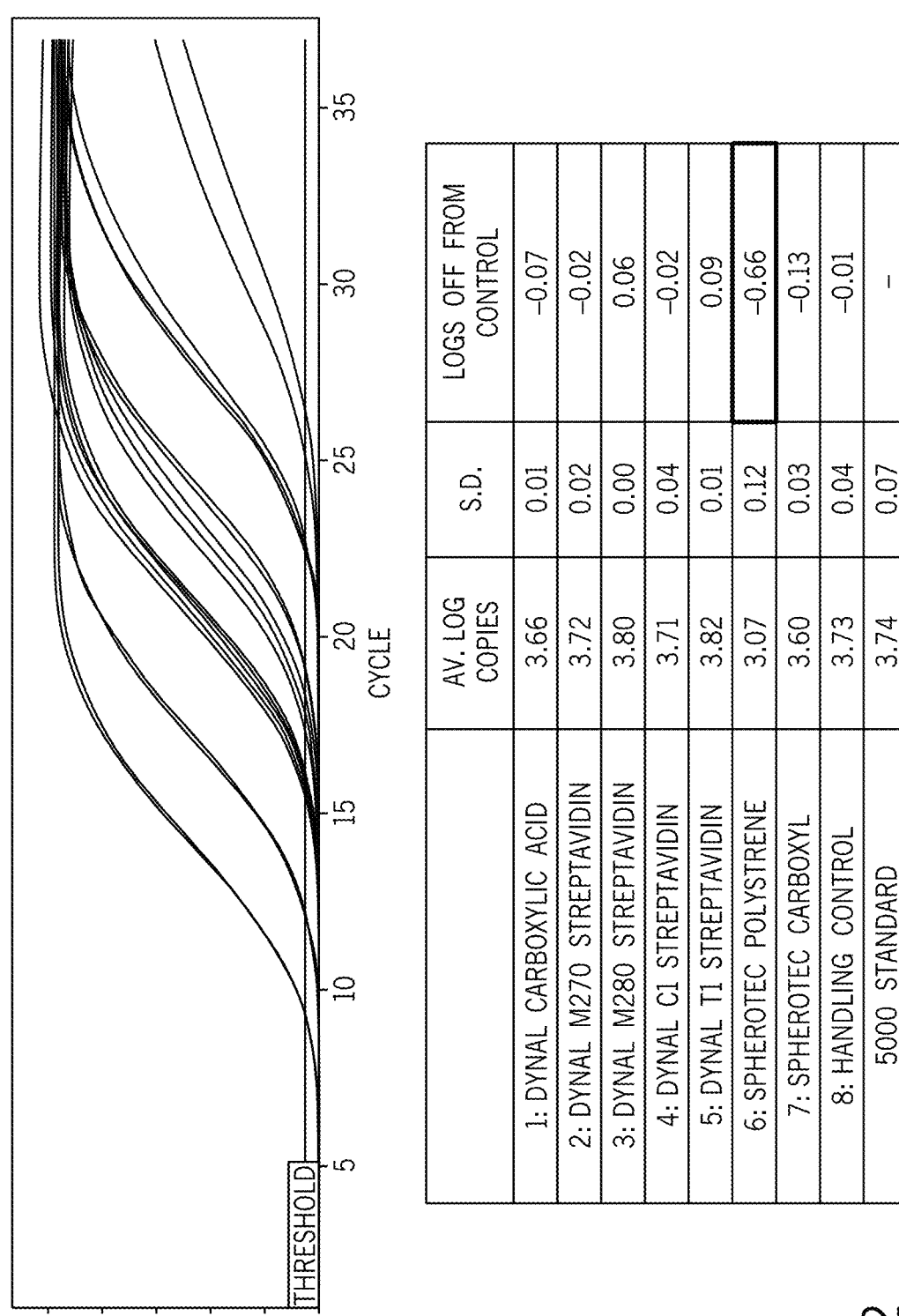
FIG. 22. Graph and table depicting enzyme activity under various conditions, in the presence and absence of paramagnetic particles.
Figure 23:
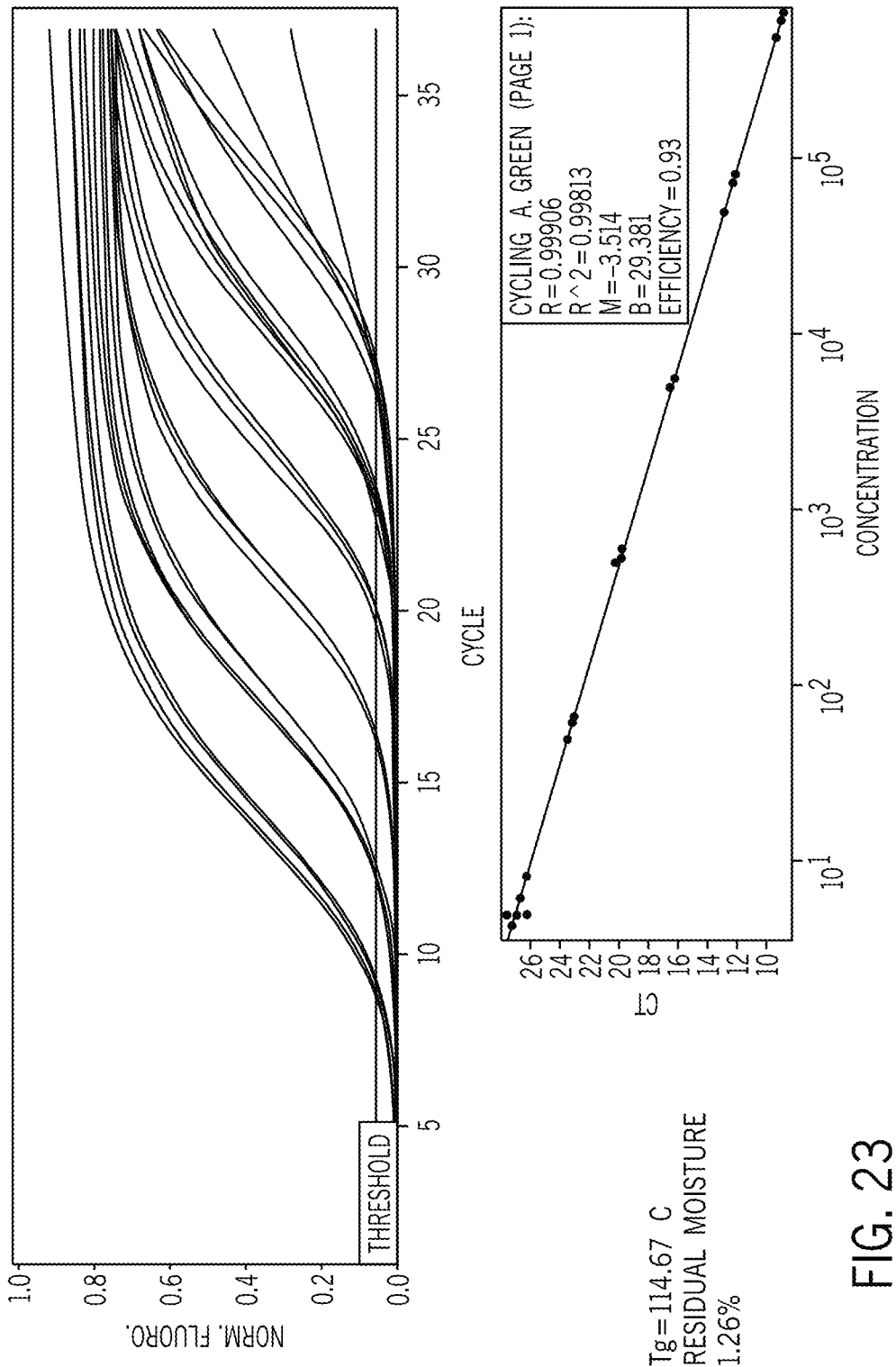
FIG. 23. Graph and table depicting the effects on enzyme activity of lyophilizing various reagents and paramagnetic particles to the sample container.

Experiments were conducted during development of embodiments herein to determine the effect of paramagnetic particles (PMPs) on assay performance within the devices and systems described herein. FIG. 22 depicts the results of experiments to test the effect of seven different PMPs and lyophilized PCR reagents on PCR effectiveness. FIG. 23 depicts the results of experiments to test the effect of lyophilizing the PMPs with the PCR reagents.

The invention claimed is:

1. A method of thermocycling a sample comprising:
   (a) placing the sample in the sample container in a cassette, wherein the cassette comprises a sample container of 1 mm or less thickness sandwiched between front and rear surfaces of 1 mm or less thickness each;

(b) holding the sample container in a stationary position;

(c) (i) moving a first pair of heaters into opposing orientations on either side of the sample container adjacent to the front and rear surfaces, respectively, and (ii) narrowing a gap between the first pair of heaters when the sample container is in the gap between the first pair of heaters, thereby creating a first temperature zone between the first pair of heaters with an entirety of the sample within the first temperature zone;

(d) (i) expanding the gap between the first pair of heaters, and (ii) moving the first pair of heaters away from the sample container, thereby removing the first temperature zone from the sample;

(e) (i) moving a second pair of heaters into opposing orientations on either side of the sample container adjacent to the front and rear surfaces, respectively, and (ii) narrowing a gap between the second pair of heaters when the sample container is in the gap between the second pair of heaters, thereby creating a second temperature zone between the second pair of heaters with an entirety of the sample within the second temperature zone;

(f) (i) expanding the gap between the second pair of heaters, and (ii) moving the second pair of heaters away from the sample container, thereby removing the second temperature zone from the sample; and (g) repeating steps (c) through (f).

2. The method of claim 1, wherein narrowing the gap between the first pair of heaters comprises contacting the front and rear front surfaces of the sample container with the first pair of heaters, and wherein narrowing the gap between the second pair of heaters comprises contacting the front and rear front surfaces of the sample container with the second pair of heaters.

3. The method of claim 1, further comprising:

(g) (i) moving a third pair of heaters into opposing orientations on either side of the sample container adjacent to the front and rear surfaces, respectively, and (ii) narrowing a gap between the third pair of heaters when the sample container is in the gap between the third pair of heaters, thereby creating a third temperature zone between the third pair of heaters with an entirety of the sample within the third temperature zone;

(h) (i) expanding the gap between the third pair of heaters, and (ii) moving the third pair of heaters away from the sample container, thereby removing the third temperature zone from the sample.

4. The method of claim 1, wherein step (g) is performed 10 or more times.

5. The method of claim 1, wherein the sample comprises a fluorescent dye, and the method further comprises a step of detecting fluorescence emission from the sample.

6. The method of claim 5, wherein fluorescence is detected while holding the sample container in a stationary position after each time the sample container is cycled through the first and second temperature zones.

7. The method of claim 1, wherein the sample container is maintained within the first and second temperatures zones for 1-5 seconds each during each cycle.

\* \* \* \* \*